US010844357B2

(12) United States Patent
Oomens

(10) Patent No.: US 10,844,357 B2
(45) Date of Patent: Nov. 24, 2020

(54) ENGINEERED RESPIRATORY SYNCYTIAL VIRUSES WITH CONTROL OF CELL-TO-CELL VIRUS TRANSMISSION FOR ENHANCED SAFETY OF LIVE VIRUS VACCINES

(71) Applicant: THE BOARD OF REGENTS FOR OKLAHOMA STATE UNIVERSITY, Stillwater, OK (US)

(72) Inventor: Antonius G. P. Oomens, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 162 days.

(21) Appl. No.: 16/030,259

(22) Filed: Jul. 9, 2018

(65) Prior Publication Data

US 2018/0320146 A1 Nov. 8, 2018

Related U.S. Application Data

(63) Continuation of application No. 14/123,444, filed as application No. PCT/US2012/040539 on Jun. 1, 2012, now abandoned.

(60) Provisional application No. 61/492,261, filed on Jun. 1, 2011.

(51) Int. Cl.

| | |
|---|---|
| ***C12N 7/00*** | (2006.01) |
| ***C07K 14/005*** | (2006.01) |
| ***C12Q 1/06*** | (2006.01) |
| *A61K 39/00* | (2006.01) |

(52) U.S. Cl.

CPC .............. *C12N 7/00* (2013.01); *C07K 14/005* (2013.01); *C12Q 1/06* (2013.01); *A61K 2039/5254* (2013.01); *A61K 2039/5258* (2013.01); *C12N 2760/18511* (2013.01); *C12N 2760/18522* (2013.01); *C12N 2760/18523* (2013.01); *C12N 2760/18534* (2013.01); *C12N 2760/18562* (2013.01); *G01N 2333/115* (2013.01); *G01N 2500/00* (2013.01)

(58) Field of Classification Search

None

See application file for complete search history.

(56) References Cited

U.S. PATENT DOCUMENTS

2003/0054505 A1* 3/2003 Jin ........................ C07K 14/005 435/110

OTHER PUBLICATIONS

Ito et al., Microbiol Innnnunol. 2005; vol. 49(11): pp. 971-979 (Year: 2005).*

Teng et al., J. Virol. vol. 72 No. 7, pp. 5707-5716, year 1998 (Year: 1998).*

* cited by examiner

*Primary Examiner* — Shanon A. Foley

*Assistant Examiner* — Myron G Hill

(74) *Attorney, Agent, or Firm* — Fellers, Snider, Blankenship, Bailey & Tippens, P.C.; Terry L. Watt

(57) ABSTRACT

Highly antigenic yet safe vaccines against diseases caused by Paramyxoviridae viruses such as respiratory syncytial virus (RSV) are provided. The vaccines comprise attenuated Paramyxoviridae viruses with high antigenicity but which display impaired cell-to-cell transmission as a result of genetic manipulation of the gene encoding the matrix (M) protein. In the viruses, the M protein is absent or mutated to a less active form. Screening or assay systems and methods for evaluating the infectivity of mutant M proteins anf for identifying suitable M candidates for live-attenuated vaccine virus and VLP production, are also provided.

15 Claims, 20 Drawing Sheets

Specification includes a Sequence Listing.

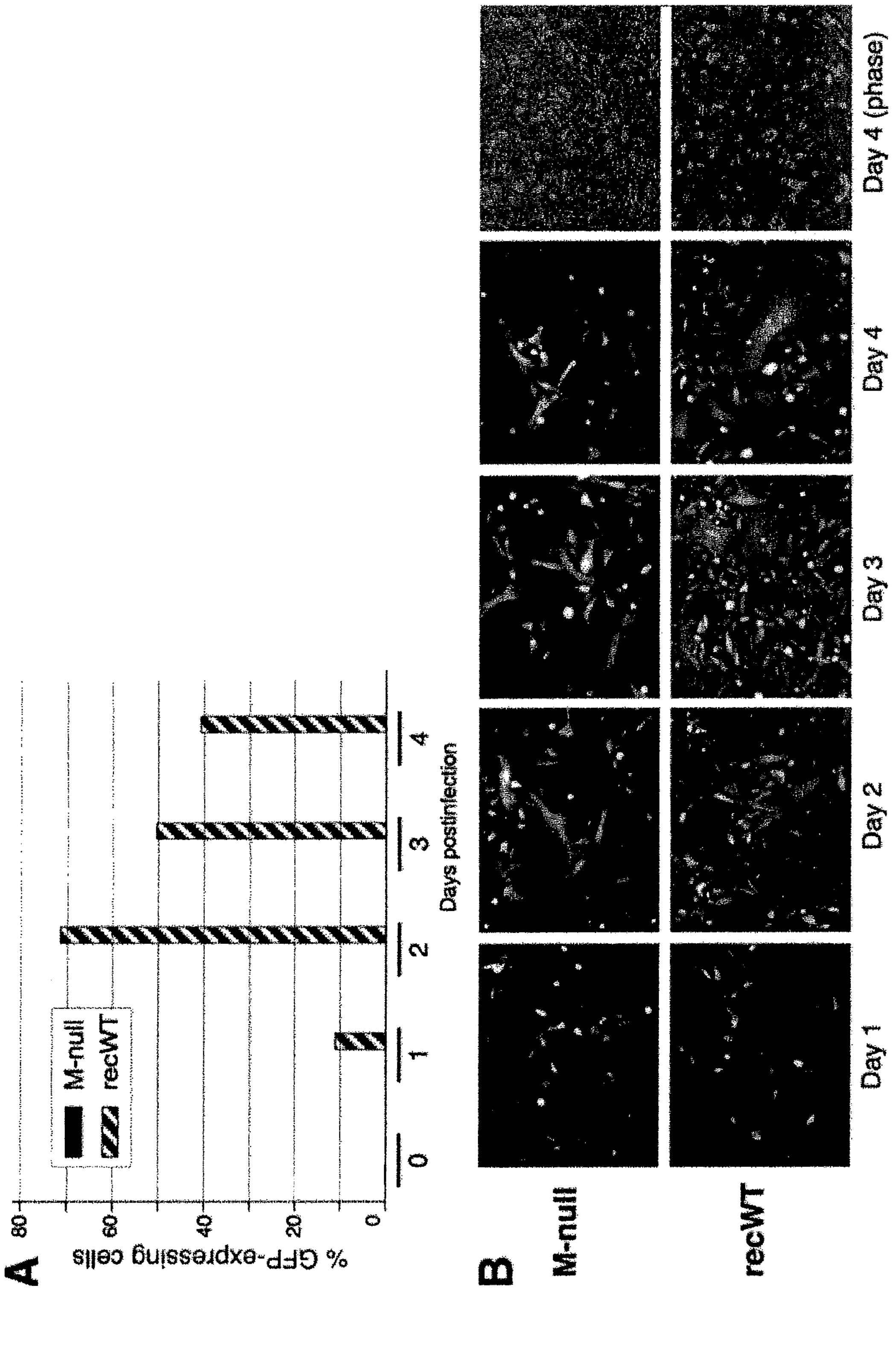
FIGURES 3A and B

A.
ATGGAAACATACGTGAACAAGCTTCACGAAGGCTCCACATACACAGCTGCTGTTCAATAC
AATGTCTTAGAAAAAGACGATGACCCTGCATCACTTACAATATGGGTGCCCATGTTCCAA
TCATCTATGCCAGCAGATTTACTTATAAAAGAACTAGCTAATGTCAACATACTAGTGAA
ACAAATATCCACACCCAAGGGACCTTCACTAAGAGTCATGATAAACTCAAGAAGTGCAG
TGCTAGCACAAATGCCCAGCAAATTTACCATATGCGCTAATGTGTCCTTGGATGAAAGAA
GCAAACTAGCATATGATGTAACCACACCCTGTGAAATCAAGGCATGTAGTCTAACATGCC
TAAAATCAAAAAATATGTTGACTACAGTTAAAGATCTCACTATGAAGACACTCAACCCT
ACACATGATATTATTGCTTTATGTGAATTTGAAAACATAGTAACATCAAAAAAAGTCAT
AATACCAACATACCTAAGATCCATCAGTGTCAGAAATAAAGATCTGAACACACTTGAAA
ATATAACAACCACTGAATTCAAAAATGCTATCACAAATGCAAAAATCATCCCTTACTCA
GGATTACTATTAGTCATCACAGTGACTGACAACAAAGGAGCATTCAAATACATAAAGCC
ACAAAGTCAATTCATAGTAGATCTTGGAGCTTACCTAGAAAAAGAAAGTATATATTATG
TTACCACAAATTGGAAGCACACAGCTACACGATTTGCAATCAAACCCATGGAAGATTAA
(SEQ ID NO: 1)

B.

ATGGAGACCTACGTGAACAAGCTGCACGAGGGCAGCACCTACACCGCCGCCGTGCAGTAC
AACGTGCTGGAGAAGGACGACGACCCCGCCAGCCTGACCATCTGGGTGCCCATGTTCCAG
AGCAGCATGCCCGCCGACCTGCTGATCAAGGAGCTGGCCAACGTGAACATCCTGGTGAAG
CAGATCAGCACCCCCAAGGGGCCTAGCCTGCGCGTGATGATCAACAGCCGCAGCGCCGTG
CTGGCCCAGATGCCCAGCAAGTTCACCATCTGCGCCAACGTGAGCCTGGACGAGCGCAGC
AAGCTGGCCTACGACGTGACCACCCCCTGCGAGATCAAGGCCTGCAGCCTGACCTGCCTG
AAGAGCAAGAACATGCTGACCACCGTGAAGGACCTGACCATGAAGACCCTGAACCCCACC
CACGACATCATCGCCCTGTGCGAGTTCGAGAACATCGTGACCAGCAAGAAAGTGATCATC
CCCACCTACCTGCGCAGCATCAGCGTGCGCAACAAGGACCTGAACACCCTGGAGAACATC
ACCACCACCGAGTTCAAGAACGCCATCACCAACGCCAAGATCATCCCCTACAGCGGCCTG
CTGCTGGTGATCACCGTGACCGACAACAAGGGCGCCTTCAAGTACATCAAGCCCCAGAGC
CAGTTCATCGTGGACCTGGGCGCCTACCTGGAGAAGGAGAGCATCTACTACGTGACCACC
AACTGGAAGCACACCGCCACCCGCTTCGCCATCAAGCCTATGGAGGACTAA
(SEQ ID NO: 2)

FIGURE 6A and B

METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED
(SEQ ID NO: 3)

FIGURE 7

A.
MSWKDASGWSETYVNKLHEGSTYTAAVQYNVLEKDDDPASLTIWVPMFQSSMPADLLI
KELANVNILVKQISTPKGPSLRVMINSRSAVLAQMPSKFTICANVSLDERSKLAYDVTTPCE
IKACSLTCLKSKNMLTTVKDLTMKTLNPTHDIIALCEFENIVTSKKVIIPTYLRSISVRNKDL
NTLENITTTEFKNAITNAKIIPYSGLLLVITVTDNKGAFKYIKPQSQFIVDLGAYLEKESIYYV
TTNWKHTATRFAIKPMED (SEQ ID NO: 4)

B.
METYVNKLHESWKDASGWSGSTYTAAVQYNVLEKDDDPASLTIWVPMFQSSMPADLLI
KELANVNILVKQISTPKGPSLRVMINSRSAVLAQMPSKFTICANVSLDERSKLAYDVTTPCE
IKACSLTCLKSKNMLTTVKDLTMKTLNPTHDIIALCEFENIVTSKKVIIPTYLRSISVRNKDL
NTLENITTTEFKNAITNAKIIPYSGLLLVITVTDNKGAFKYIKPQSQFIVDLGAYLEKESIYYV
TTNWKHTATRFAIKPMED (SEQ ID NO: 5)

C.
MAAYVNKLHEGSTYTAAVQYNVLEKDDDPASLTIWVPMFQSSMPADLLIKELANVNILV
KQISTPKGPSLRVMINSRSAVLAQMPSKFTICANVSLDERSKLAYDVTTPCEIKACSLTCLK
SKNMLTTVKDLTMKTLNPTHDIIALCEFENIVTSKKVIIPTYLRSISVRNKDLNTLENITTT
EFKNAITNAKIIPYSGLLLVITVTDNKGAFKYIKPQSQFIVDLGAYLEKESIYYVTTNWKHT
ATRFAIKPMED (SEQ ID NO: 6)

D.
METAANKLHEGSTYTAAVQYNVLEKDDDPASLTIWVPMFQSSMPADLLIKELANVNILV
KQISTPKGPSLRVMINSRSAVLAQMPSKFTICANVSLDERSKLAYDVTTPCEIKACSLTCLK
SKNMLTTVKDLTMKTLNPTHDIIALCEFENIVTSKKVIIPTYLRSISVRNKDLNTLENITTT
EFKNAITNAKIIPYSGLLLVITVTDNKGAFKYIKPQSQFIVDLGAYLEKESIYYVTTNWKHT
ATRFAIKPMED (SEQ ID NO: 7)

E.
METYVAALHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 8)

F.
METYVNKAAEGSTYTAAVQYNVLEKDDDPASLTIWVPMFQSSMPADLLIKELANVNILV
KQISTPKGPSLRVMINSRSAVLAQMPSKFTICANVSLDERSKLAYDVTTPCEIKACSLTCLK
SKNMLTTVKDLTMKTLNPTHDIIALCEFENIVTSKKVIIPTYLRSISVRNKDLNTLENITTT
EFKNAITNAKIIPYSGLLLVITVTDNKGAFKYIKPQSQFIVDLGAYLEKESIYYVTTNWKHT
ATRFAIKPMED (SEQ ID NO: 9)

FIGURE 8 A-F

A.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACAATCLKS
KNMLTTVKDLTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 10)

B.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLAALKS
KNMLTTVKDLTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 11)

C.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCAAS
KNMLTTVKDLTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 12)

D.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKA
ANMLTTVKDLTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 13)

E.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KAALTTVKDLTMKTLNPTHDIIALCEFENIVTSKKVIIPTYLRSISVRNKDLNTLENITTTEF
KNAITNAKIIPYSGLLLVITVTDNKGAFKYIKPQSQFIVDLGAYLEKESIYYVTTNWKHTAT
RFAIKPMED (SEQ ID NO: 14)

F.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMAATVKDLTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 15)

Figure 9A-F

G.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTAAKDLTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 16)

H.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVAALTMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 17)

I.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDAAMKTLNPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 18)

J.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTAATLNPTHDIIALCEFENIVTSKKVIIPTYLRSISVRNKDLNTLENITTTEF
KNAITNAKIIPYSGLLLVITVTDNKGAFKYIKPQSQFIVDLGAYLEKESIYYVTTNWKHTAT
RFAIKPMED (SEQ ID NO: 19)

K.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKAANPTHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 20)

L.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLAATHDIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 21)

Figure 9 G-L

M.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPAADIIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 22)

N.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHAAIALCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 23)

O.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHDIAGLCEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 24)

P.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHDIIAAAEFENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 25)

Q.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHDIIALCAAENIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 26)

R.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHDIIALCEFAAIVTSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 27)

Figure 9 M-R

S.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHDIIALCEFENAATSKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 28)

T.
METYVNKLHEGSTYTAAVQYNVLEKDDDPASLTIWVPMFQSSMPADLLIKELANVNILVK
QISTPKGPSLRVMINSRSAVLAQMPSKFTICANVSLDERSKLAYDVTTPCEIKACSLTCLKS
KNMLTTVKDLTMKTLNPTHDIIALCEFENIVAAKKVIIPTYLRSISVRNKDLNTLENITTTE
FKNAITNAKIIPYSGLLLVITVTDNKGAFKYIKPQSQFIVDLGAYLEKESIYYVTTNWKHTA
TRFAIKPMED (SEQ ID NO: 29)

Figure 9 S and T

ENGINEERED RESPIRATORY SYNCYTIAL VIRUSES WITH CONTROL OF CELL-TO-CELL VIRUS TRANSMISSION FOR ENHANCED SAFETY OF LIVE VIRUS VACCINES

CROSS REFERENCE TO RELATED APPLICATION

This application claims the benefit of U.S. Provisional Application No. 61/492,261 filed Jun. 1, 2011, herein incorporated by reference in its entirety for all purposes.

SEQUENCE LISTING

This application includes as the Sequence Listing the complete contents of the accompanying text file "Sequence.txt", created Jun. 1, 2011, containing 64,808 bytes, hereby incorporated by reference.

DESCRIPTION

Background of the Invention

Field of the Invention

The invention generally relates to vaccines against diseases caused by Paramyxoviridae viruses such as respiratory syncytial virus (RSV), as well as Retroviridae members and Mononegavirales order members. In one embodiment, the invention provides attenuated Paramyxoviridae which display high antigenicity but are nevertheless safe for use in vaccines due to their low level of cell-to-cell transmission, as a result of genetic manipulation of the gene encoding the matrix (M) protein, and to methods of identifying suitable M protein modifications.

Background of the Invention

Human respiratory syncytial virus (RSV, the type species of the genus Pneumovirus within the family Paramyxoviridae) is a major cause of severe lower respiratory tract disease in infants, children, immunosuppressed individuals and the elderly. In the United States, 60% of infants are infected with RSV during their first season of exposure to the virus, and nearly all children will have been infected with the virus by 2-3 years of age. Of those individuals infected with RSV, which includes increasing numbers of the elderly, 2-3% will develop bronchiolitis and require hospitalization. In fact, RSV is the largest viral cause of pediatric bronchiolitis worldwide. Treatment of bronchiolitis is limited to supportive care such as oxygen therapy, and the virus causes over 100,000 deaths per year worldwide. Natural infection with RSV fails to induce a fully protective immune response. Moreover, this immunity wanes over time, possibly more so than does that of other respiratory viral infections. Thus, people can be infected multiple times, and sometimes an infant can become symptomatically infected more than once, even within a single RSV season and with the same strain.

Although several attempts have been made, no vaccine against RSV is currently available and the development of vaccines for RSV has proven to be extremely challenging. For live-attenuated vaccines in general, the typical procedure is to produce a weakened virus which is administered to a vaccine recipient. The attenuated virus infects and spreads to a number of host cells, thereby mimicking a natural infection. The goal is to elicit a strong, protective immune response by the host (efficacy) without causing the side effects of the natural virus (safety), and the balance of efficacy/safety is critical. Viral replication-related factors that determine efficacy include the level of virus replication and thus viral antigen production in infected cells, and the extent to which the virus spreads to neighboring cells and disseminates within the host. The extent of live virus dissemination within the host is also one of the main factors that determine vaccine safety, as viral replication was shown to be a predictor of disease severity (C. M. El Saleeby et al, 2011, J. Infect. Dis. 2004; T P Welliver et al, 2008, Pediatr. Infect. Dis. J. 27). Minimal side effects (safety) are a large concern for any vaccine in a very young age group, and this is especially true for children with underlying conditions such as asthma. In the current live vaccine approaches, safety (reduction of side effects) is based on reducing the ability of the viral genomic RNA to replicate itself. This is generally accomplished by introducing point mutations in the human RSV genome or by using RSV from other species (e.g., bovine) which do not replicate their RNA genome effectively in a human host. However, the results of clinical trials indicate that the balance of efficacy to safety is very difficult to achieve with these approaches. In part, this is due to the principle by which safety is provided: by mutating the viral RNA to downregulate genomic replication, viral antigen production (which is dependent on viral replication and transcription) is also inadvertently downregulated. A second approach also aimed at downregulating the level of viral genome replication, involves the use of heterologous viral backbones which do not replicate well in humans such as bovine RSV or Newcastle Disease virus (NDV), in which some of the human RSV genes are inserted as antigens. This approach too results in lowered replication levels and thereby lower antigen production levels.

One previous attempt to vaccinate young children against RSV employed a parenterally administered formalin-inactivated RSV vaccine. Unfortunately, administration of this vaccine in several field trials was shown to be associated with the development of a significantly exacerbated illness following subsequent natural infection with RSV. Following the lack of success with the formalin-inactivated RSV vaccine, emphasis has been placed on other methods including the development of live attenuated vaccines, which do not show the exacerbated disease symptoms experienced with inactivated virus vaccine. However, previous and current vaccine efforts (generally based on attenuation of viral RNA replication, either by point mutations or by using heterologous backbones, see above) have experienced great difficulty in finding the proper balance of efficacy and safety.

RSV contains a negative-sense, single-stranded RNA genome that expresses eleven known proteins from ten genes. Of these, the G (attachment), and F (fusion) proteins have been characterized as transmembrane glycoproteins and contain the major antigenic epitopes of human respiratory syncytial virus. U.S. Pat. No. 7,588,770 to Oomens et al., the entire contents of which is hereby incorporated by reference, describes genetically modified RSVs generated by replacing genes encoding proteins such as F and G with genes encoding heterologous envelope proteins, e.g., a baculovirus GP64 envelope glycoprotein. Such genetically modified RSVs exhibit improved temperature stability and in some cases are infectious but incapable of cell-to-cell transmission. Thus, these attenuated viruses are safe for use in vaccines. However, a disadvantage of this technology is that removal of the F and G proteins from the virus greatly reduces antigenicity, thereby decreasing the ability of the viruses to elicit a robust, protective immune response. In addition, the level of cell-to-cell transmission of these viruses cannot be tuned up or down to a desired or preferred balance of efficacy and safety.

The prior art has thus far failed to provide an RSV (or other Paramyxoviridae) which solves the dilemma of needing a virus that is used in a vaccine to be both highly antigenic and yet safe for administration, e.g., through controlled dissemination within the lung.

SUMMARY OF THE INVENTION

To overcome the limitations of prior art approaches, this application describes a system in which vaccine safety is not provided by lowering replication levels, but by controlling cell-cell transmission. As a consequence of not being attenuated in replication/transcription, high levels of RSV antigens will be produced, while control of cell-cell transmission (and thus virus dissemination) provides safety features to prevent live vaccine virus from excessive dissemination.

The invention provides vaccines comprising Paramyxoviridae viruses, as well as Retroviridae or other Mononegavirales members, which are safe for use in vaccines. This invention was designed to improve the efficacy/safety balance by imparting safety based on control of virus dissemination. The viruses were developed using genetic engineering methodology that directly controls cell-to-cell transmission of the virus through manipulation of the essential viral protein, Matrix (M). Viral matrix proteins are structural proteins linking the viral envelope with the virus core, and the invention involves genetic manipulation of such matrix proteins to render them inactive, and/or to exhibit a desired lower (lessened, decreased, diminished, etc.) level of activity, e.g., when compared to M of a comparable wild type virus. Data presented herein show that virus dissemination to neighboring cells can be blocked entirely or, alternatively, fine-tuned to different desirable levels, by genetically manipulating the gene encoding M protein so that in the virus, the M protein is absent, non-functional, or attenuated so as to function at a desired low level. This novel means of controlling viral transmission is thus independent of the level of RNA replication, and RNA replication remains normal or near normal in the recombinant virus. In the complete absence of M (M-null), viral protein levels are in fact higher than those seen with a wild type (i.e., "wt") virus (see FIG. 2B of Example 1), probably due to the known inhibitory effect of the M protein on replication and transcription. Thus, normal or above normal levels of replication/transcription by viruses expressing modified M proteins results in the production of large amounts of antigens when the virus infects host cells. When the virus is administered to a subject as a vaccine, the subject should then mount a vigorous immune response to the antigens produced in infected host cells. However, because cell-to-cell transmission of the virus is impaired or controlled, the development of a full blown viral infection (including dissemination within the lung) is precluded (or at least lessened), making the vaccine safe for administration. In other words, the genetically modified viruses are able to infect host cells at or near the site or location of administration, (i.e., they infect the cells that they encounter in a localized area) but the infection does not tend to spread further, or is at least circumscribed within or close to the initial area of administration; for example, it will not disseminate to the lower respiratory tract (LRT) when applied to the upper respiratory tract (URT).

The invention provides recombinant, live attenuated viruses in which a gene encoding a matrix (M) protein is i) deleted; ii) genetically manipulated to produce an M protein with no or decreased activity; or iii) genetically manipulated to produce a decreased amount of said M protein. In some embodiments, the recombinant, live attenuated virus is a Paramyxoviridae virus, for example, a Pneumovirus virus such as a respiratory syncytial virus (RSV). In some embodiments, the RSV is human RSV. In some embodiments the recombinant, live attenuated virus will be a member of the group consisting of RNA viruses, Mononegavirales order viruses, Paramyxoviridae viruses and retroviruses.

The invention also provides pharmaceutical compositions comprising the recombinant, live, attenuated virus described above in an amount sufficient to elicit an immune response in a host, as well as a method of immunizing a subject against symptoms of disease caused by, for example, a Paramyxoviridae virus by administering to said subject at least one dose of the pharmaceutical composition to the subject. In some embodiments, the Paramyxoviridae virus is RSV and the subject is selected from the group consisting of a child, an immunocompromised individual, and an elderly individual.

The invention also provides viral replication assessment systems, comprising 1) a host cell comprising nucleic acid (nucleotide) sequences comprising a transcriptional control element operably linked to nucleic acid sequences encoding a mutant M protein; and 2) an M-null virus. In some embodiments, the transcriptional control element is a constitutive promoter, for example, a cytomegolovirus (CMV) promoter. In other embodiments, the transcriptional control element is inducible and the M-null virus comprises nucleic acid sequences encoding at least one gene product capable of activating the inducible transcriptional control element. In further embodiments, the inducible transcriptional control element comprises tetracycline response elements (TRE) and at least one gene product is tetracycline transactivating protein (Tet). In some embodiments, nucleic acid sequences comprising an inducible transcriptional control element are present at a location selected from the group consisting of: within a virus; on a plasmid; on a mini-replicon; and within the host cell genome. In some embodiments, the virus is a Paramyxoviridae virus. In other embodiments, the mutant M protein is a double alanine mutant M protein.

The invention further provides methods of assessing viral replication, comprising the steps of 1) providing a plurality of host cells, each of which comprises nucleic acid sequences comprising a transcriptional control element operably linked to nucleic acid sequences encoding said mutant M protein; infecting at least one of said plurality of host cells with at least one M-null virus; and measuring a titer of viral progeny produced in said plurality of host cells. The host cells may be any type of cell which is capable of being infected by the virus that is being tested, or by a wild type (non-mutant) version of the virus being tested, or which allows viral replication of non-mutant wild type viruses. In some embodiments, the transcriptional control element is a constitutive promoter such as cytomegolovirus (CMV) promoter. In other embodiments, the transcriptional control element is inducible and the M-null virus comprises nucleic acid sequences encoding at least one gene product capable of activating the inducible transcriptional control element. In some embodiments, the inducible transcriptional control element comprises tetracycline response elements (TRE) and the at least one gene product is tetracycline transactivating protein (Tet).

In other embodiments, the nucleic acid sequences comprising an inducible transcriptional control element are present at a location selected from the group consisting of: within a virus (e.g., located in a viral genome); on a plasmid; on a mini-replicon; and within the host cell genome. In one embodiment, the virus is a Paramyxoviridae virus. In some embodiments, the mutant M protein is a double alanine mutant M protein.

The invention also provides methods of identifying M protein mutations that alter infectious virus production, comprising the steps of 1) providing a plurality of host cells, each of which comprises nucleic acid sequences comprising a transcriptional control element operably linked to nucleic acid sequences encoding an M protein with a mutation; 2) infecting at least one of said plurality of host cells with at least one M-null virus; measuring a titer of viral progeny produced in said plurality of host cells; and if said titer of viral progeny differs from a control titer of viral progeny obtained with wild type virus, then identifying said mutation in said M protein as including an M protein mutation that alters infectious virus production. In some embodiments, when the titer of viral progeny is less than (decreased compared to) a control titer of viral progeny obtained with wild type virus, then the mutation in the M protein is identified as an M protein mutation that decreases infectious virus production. In other embodiments, when the titer of viral progeny is greater than the control titer of viral progeny obtained with wild type virus, then the mutation in the M protein is identified as an M protein mutation that increases infectious virus production.

The invention also provides methods of making a virus with a decreased capacity for virus production compared to a wild type control virus, comprising the steps of 1) providing a plurality of host cells, each of which comprises nucleic acid sequences comprising a transcriptional control element operably linked to nucleic acid sequences encoding an M protein with a mutation; 2) infecting at least one of said plurality of host cells with at least one M-null virus; 3) measuring a titer of viral progeny produced in said plurality of host cells; and, if said titer of viral progeny is less than a control titer of viral progeny obtained with wild type virus, then 3) identifying the mutation in the M protein as a mutation that decreases infectious virus production; and 4) genetically engineering a virus to contain and express nucleic acid sequences encoding the M protein with the mutation.

BRIEF DESCRIPTION OF THE DRAWINGS

FIGS. 3A and B. Viral replication in cell culture in the absence of M. (A) Flow cytometry. HEp-2 cells were infected with viruses M-null or recWT by adding inoculum (~0.2 PFU/cell) and centrifugation for 10 min at 3,000×g. Immediately after infection and at 1-day intervals, progeny virus was harvested by scraping cells into the medium and transferring the samples to −80° C. Frozen samples were thawed, mixed by gentle pipetting, cleared by low-speed centrifugation, and used to infect freshly plated (receiver) HEp-2 cells. At 24 hpi, receiver cells were trypsinized, fixed with 4% paraformaldehyde in suspension, and the percentage of GFP-expressing cells was determined with flow cytometry. The data represent the average value of duplicate samples. (B) HEp-2 cells were similarly infected with viruses M-null (top panels) or recWT (bottom panels). At day 1, 2, 3, and 4 postinfection, GFP expression within the infected cultures was examined on a fluorescence microscope, and photographed at a magnification of 100×. A phase-contrast image of day 4 postinfection was also included (Day 4 (phase)).

FIGS. 6A and B. A, Sequence of the (unmodified) M gene from RSV A2 strain (SEQ ID NO: 1); B, Sequence of the codon-optimized M gene used to generate M-expressing cells (SEQ ID NO: 2). SEQ ID NOS: 1 and 2 encode exactly the same protein.

FIG. 7. Amino acid sequence of unmodified M protein (SEQ ID NO: 3).

FIG. 8A-F. Examples of scan mutations. A-B: Exemplary epitope scan mutations; C-F: Exemplary alanine scan mutations.

FIG. 9A-T. Exemplary alanine scan mutations. A, M protein with alanine substitution at positions 116/117 (SEQ ID NO 10); B, M protein with alanine substitution at positions 118/119 (SEQ ID NO 11); C, M protein with alanine substitution at positions 120/121 (SEQ ID NO: 12); D, M protein with alanine substitution at positions 122/123 (SEQ ID NO: 13); E, M protein with alanine substitution at positions 124/125 (SEQ ID NO: 14); F, M protein with alanine substitution at positions 126/127 (SEQ ID NO: 15); G, M protein with alanine substitution at positions 128/129 (SEQ ID NO: 16); H, M protein with alanine substitution at positions 130/131 (SEQ ID NO: 17); I, M protein with alanine substitution at positions 132/133 (SEQ ID NO: 18); J, M protein with alanine substitution at positions 134/135 (SEQ ID NO: 19); K, M protein with alanine substitution at positions 136/137 (SEQ ID NO: 20); L, M protein with alanine substitution at positions 138/139 (SEQ ID NO: 21); M, M protein with alanine substitution at positions 140/141 (SEQ ID NO: 22); N, M protein with alanine substitution at positions 142/143(SEQ ID NO: 23); O, M protein with alanine/glycine substitution at position 144/145 (SEQ ID NO: 24) (NOTE that residue 145 already is alanine in wt M and therefore was changed to glycine); P, M protein with alanine substitution at positions 146/147 (SEQ ID NO: 25); Q, M with alanine substitution at position 148/149 (SEQ ID NO: 26); R, M protein with alanine substitution at positions 150/151 (SEQ ID NO: 27); S, M protein with alanine substitution at positions 152/153 (SEQ ID NO: 28); T, M with alanine substitution at position 154/155:(SEQ ID NO: 29).

DETAILED DESCRIPTION

Figure 1A:
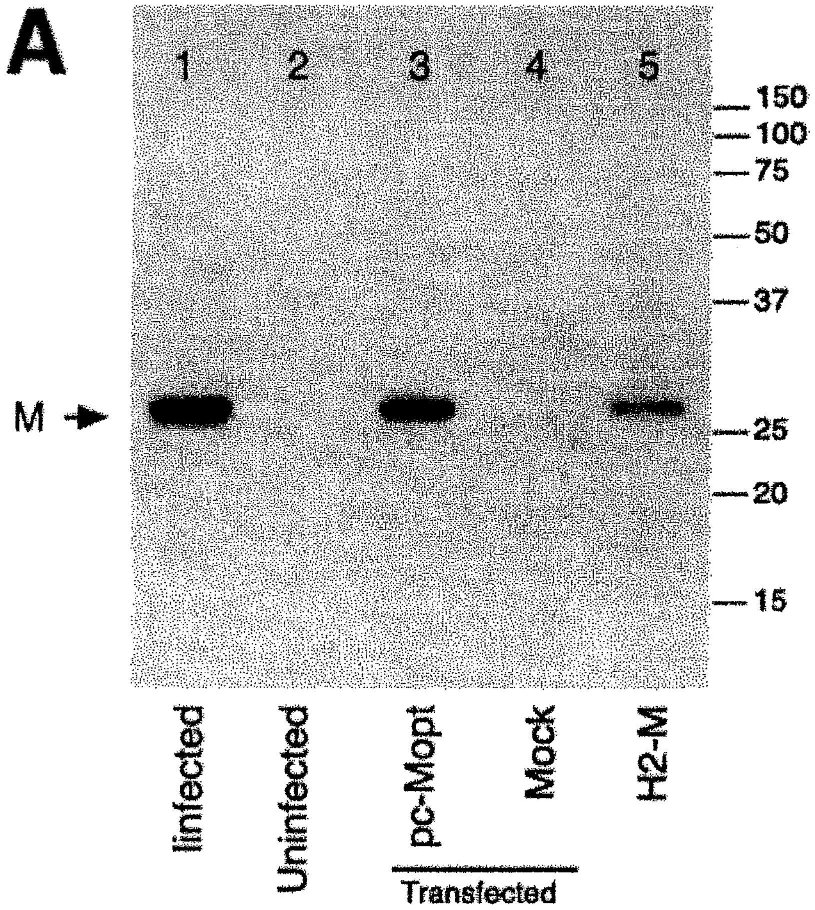
FIG. 1A-C. Transient and stable expression of the M protein from a codon-optimized ORF. (A) Western blot analysis. Lysates of transfected HEp-2 cells were prepared at 30 hpx and a western blot was generated after SDS-PAGE under reducing conditions. Lane 3 represents cells transfected with a plasmid expressing M from a codon-optimized ORF (pc-Mopt). As controls, lysates with equivalent cell numbers of mock transfected cells (lane 4), wt virus infected cells (lane 1), and uninfected cells (lane 2) were included. (For lane 5, see FIG. 1C). The position of molecular weight markers and the M protein are indicated. (B) Transient expression of M by IF microscopy. pc-Mopt transfected cells (panels 2 and 3) or mock-transfected cells (panel 1) on glass coverslips were fixed and permeabilized at 30 hpx, and incubated with anti-M peptide serum and alexa-488 conjugated anti-rabbit antibodies. Samples were examined on a fluorescent microscope and photographed at 600× magnification. Panels 2 and 3 represent differential expression patterns observed within the same sample. (C) Analysis of M-expressing cell line H2-M. Tet-responsive H2-M cells were induced for M expression by adding doxycyclin (DOX) to the medium (panels 3 and 4, +DOX), or to left uninduced (panels 1 and 2, −DOX), and cells were fixed and permeabilized 30 hours after induction. M was visualized as described for FIG. 1B (panels 2 and 4) and cells were counterstained with DAPI to visualize nuclei (panels 1 and 3). The samples were examined on a fluorescent microscope and photographed at 200× magnification. A lysate of induced H2-M cells at 30 hours post-induction was also examined by western blot (FIG. 1A, lane 5).

The Examples presented herein show the feasibility of generating infectious virus without, or with decreased, M protein expression, or which express M proteins with activity that is less than that of wild type M protein. The Examples further describe the elucidation of the mechanism of action of the M protein of human RSV, the type species of the subfamily pneumovirinae within Paramyxoviridae. Briefly, it has been discovered that the M protein is essential for production of mature viral surface filaments and for virus infectivity. This knowledge has enabled the development of recombinant, live-attenuated, genetically engineered viruses which are fully antigenic in host cells (i.e., they contain and express genes encoding major Paramyxoviridae antigens such as G and F proteins) but which are unable or have only a limited ability to transmit progeny to other cells. Thus, the infection they cause is localized at or near the site of infection, e.g., the site at which they are administered. Because a correlation has been demonstrated between the extent of viral replication/dissemination and RSV disease severity, said viruses (which do not, or to a lesser degree, disseminate after administration) are predicted to be safer and to result in no or limited pathological side effects.

Advantages of this approach to vaccine development include but are not limited to:

a. This approach offers, independent of the level of RNA genome replication, novel options for control of virus cell-to-cell transmission, improving vaccine safety. Virus transmission to neighboring cells is blocked or controlled to a desired level, ensuring safety. Being able to achieve vaccine candidates with a range in cell-cell transmission can be important because it allows the transmission level to be raised if a stronger immune response is needed, or lowered if side effects need to be reduced. M can be rendered completely non-functional, or be excluded from the viral genome altogether, if unusually stringent safety conditions are needed for the general population or for patients with underlying conditions. With the prevalence of asthma on the rise, stringent safety features are likely to be an important consideration in future RSV vaccines.

b. RNA genome replication does not need to be attenuated, ensuring a high level of viral antigen production in cells initially infected after vaccine application. In the absence of M, and by extrapolation for any M mutants that have lost the ability to inhibit replication/transcription, viral antigen production is actually higher than wt levels (see FIG. 2 of Example 1).

c. Despite the absence or modification of M, FIGS. 4 and 5 indicate that the important G and F antigens are presented at the cell surface in a manner indistinguishable from that seen in a wild-type RSV strain, suggesting that the quality of antigen presentation will be sufficient.

d. In contrast to some approaches using non-human viral vectors, this virus remains entirely human, ensuring a broader, protective immune response.

e. The vaccine viruses of this approach can be applied intranasally if desired, mimicking the natural route of infection and allowing antigen presentation at both mucosal and systemic sites.

f. The vaccine viruses of this approach are live viruses. Live-attenuated vaccines do not cause enhanced disease, as was observed in the infamous RSV vaccine trial of the 1960s.

g. Without being bound by theory, it appears that M protein has multiple functions related to virus production, suggesting that there will be options to control cell-to-cell spread based on differential mechanisms, which in turn promises further fine tuned control over virus spreading.

h. Without being bound by theory, the RSV M protein, as the only viral protein known to target to the host nucleus, may be responsible for RSV-induced immune or cell cycle dysregulation occurring at the level of the host nucleus. The screening system elaborated in section Example 2 is well suited to identify the domains of M involved in host dysregulation in a viral context (as well as any domains of M that mediate host dysregulation in the cytoplasm). Identification of the relevant M domains allows generation of M-mutant RSV vaccine viruses attenuated in their ability to dysregulate host immunity or the host cell cycle.

The live, recombinant, attenuated viruses of the invention are produced by genetically engineering the gene encoding the M protein, and/or by genetically engineering portions of the viral genome which affect the gene encoding the M protein. In some embodiments of the invention, the gene is deleted and/or mutated so that no active M protein is produced by the viruses. However, in this embodiment, the virus is still capable of producing viral proteins other than M at a high level (e.g., antigens such as G and F, as well as other antigens and/or epitopes), but the viral proteins that are produced cannot generate infectious viral progeny. As a result, the initial infection is (largely) confined to the cells which were initially infected by the recombinant viruses that were administered in the dose of vaccine. In other words, the initial infection is circumscribed and does not spread to other cells, yet in the initially infected cells, high levels of antigenic proteins are produced and the G and F proteins are presented at the infected cell surface, with the potential to induce a strong immune response by the host.

In other embodiments of the invention, a gene encoding the M protein is still present in the viruses but is mutated in a manner that results in impaired production of the M protein, or in production of an attenuated M protein. For example, the M protein may be produced in a form that is less active, less efficient, less accurate in function, less able to target to the appropriate subcellular location, e.g., at facilitating nucleocapsid transit from viral inclusion bodies, interaction with the cellular cytoskeleton, virion budding, virion maturation, virion entry, etc. As a result, fewer virions are assembled, and/or virions are assembled more slowly, and/or the assembled virions are somehow compromised (e.g., are less capable of cell-to-cell transmission, e.g., due to a diminished ability to escape a host cell and/or a diminished ability to enter an uninfected host cell and establish an infection therein, etc.). Using entry-defective M proteins can also be used as a deliberate strategy: such viruses would continue to make viral particles (which is useful to gain vaccine efficacy) but these particles will fail to enter and/or fail to start a productive infection after entry. For example, the virions may be unstable (e.g., temperature sensitive to either heat or cold, pH sensitive, or assembled in a manner that decreases their ability to escape from infected cells and/or to bind to and enter cells and infect them, etc). In this embodiment of the invention, it is in fact possible to fine tune viral infective capability to a desired level, usually a desired low level, which results in a minimal or limited but desirable spread of the viral infection. By allowing a minimal low level of infection to occur, the production of virus particles with suitable antigenicity is prolonged and/or otherwise augmented, providing the host immune system with increased opportunity to recognize and react to the presence of viral antigens. By the "infective capability" or "infectivity" of the virus is meant the ability of progeny of the attenuated virus particles that are administered to spread to neighboring cells which were not initially infected, and to establish an infection in those cells, i.e., to create or produce additional viral progeny which are also capable of infecting host cells. Generally, the infective capability of the attenuated viruses of the invention is reduced to at least about 50% or less of that of a non-M protein attenuated reference virus; preferably to at least about 45%, 40%, 35%, 30%, or even 25% or less of that of a non-M protein attenuated reference virus; and most preferably to less than about 25%, 20%, 15%, 10% or 5% or less (e.g., even 0%) of that of a non-M protein attenuated reference virus. The "non-M protein attenuated reference virus" may be, for example, a corresponding (e.g., same species and/or same strain) wild type virus, or a corresponding virus that has been cultured in a laboratory and/or extensively characterized and hence reasonably well known in the art, or a corresponding virus that has been somehow genetically manipulated so as not to be strictly "wild type" but also not changed in a manner that effects M-protein function, etc. Those of skill in the art are well acquainted with methods for measuring the relative infectivity of diseases caused by organisms such as viruses. Such methods may involve in vitro assays which detect the spread of the virus using any of several suitable parameters (e.g., detection of virus release into medium and/or of infection of cells evidenced by changes in cell morphology, viability, etc. using staining or microscopic techniques; or measuring the amount and/or location of protein and/or nucleic acid that is produced by or associated with the virus, counting virus particles, etc.). Alternatively, such methods may involve in vivo monitoring of the effects of viral administration, e.g., in a suitable animal model or in clinical trials. In this case, gross symptoms of disease may be monitored in vaccine recipients (e.g., life span, symptoms of viral infection such as fever, nausea, diarrhea, respiratory distress, etc.), or post mortem observation of affected tissues or organs (inflammation in the respiratory tract, immune cell infiltration into the lung, titration of virus harvested from lung homogenates) may be used to establish the relative infectivity of the viruses of the invention, in comparison to a suitable reference virus.

As described above, in some embodiments of the invention the M protein is mutated to attenuate its activity (e.g., efficiency in catalyzing viral assembly, etc.). Such mutation may take any form or be carried out in any manner known to those of skill in the art, e.g., point mutations within the gene, the insertion of stop codons, truncations from the amino and/or carboxyl termini of the protein, deletion of internal portions of the gene such as of one or more sections (or portions thereof) encoding one or more functional domains, etc. Particular areas of the protein which might be targeted include but are not limited to, for example, the amino-terminus as well as the flexible hinge region in the middle of the protein (preliminary data suggests involvement in viral filament production), the region of residues 209-236 (preliminary data suggest involvement in subcellular targeting or stability of the protein, the region surrounding residue 29 (preliminary data indicate increased surface expression of the M protein). With respect to deletions, typically regions or sections with a length of about 30, 25, 20, 15, 10, 5 or even fewer (e.g., 4, 3, 2, or 1) amino acids may be deleted, e.g., the entire region of residues 209-236 may be deleted, or one or more sections within the region may be deleted. The same is true for the regions surrounding residue 29, where portions which encompass residue 29, and which may flank residue 29, or include residue 29 at the amino or carboxyl terminus, of a size of about 30, 25, 20, 15, 10, 5 or even fewer (e.g., 4, 3, 2, or 1) amino acids may deleted. Similarly, with respect to mutations, one or more mutations may be inserted within similarly sized regions of, e.g., the region of residues 209-236, the region of residue 29, or other regions of interest in the M protein, etc.

In yet other embodiments, the function of the M protein is not impaired but the amount of M protein that is produced is attenuated. For example, the gene encoding the M protein may be altered so that its transcription and/or translation is less efficient, and/or control elements that are necessary for or which facilitate transcription and/or translation may be removed (e.g., enhancers or promoters may be deleted), or mutated to be less efficient, etc.

In some embodiments of the invention, the activity of the M protein is completely abolished. Those of skill in the art will recognize that techniques which are the same or similar to those described above, may be used to completely eliminate M protein function, i.e., the gene may not necessarily be completely deleted to ablate its function. The introduction of point mutations, stop codons, deletion of portions of the gene, etc. may also suffice to completely abolish M protein activity (as described for the M-null virus, see below).

In some embodiments of the invention, the mutations that are present in the M protein are scan mutations. Those of skill in the art are familiar with scan mutation techniques, which are described in detail in Example 2 below. Briefly, scan mutations replace selected amino acids in the primary sequence of a protein with different amino acids, usually sequentially along the length of the protein sequence, and the effects of the replacement/substitution are assessed. This technique can be used, e.g., to identify residues or sections of the protein that are required or important for a particular function or activity of the protein. Exemplary scanning techniques include but are not limited to epitope scanning in which a relatively short, e.g., about 5-10 amino acid sequence (e.g., that of an epitope) is inserted at random or selected locations; the more specific single or double alanine scanning, in which each (or selected) amino acid residues of a protein sequence of interest are replaced with alanine, etc. Consecutive adjacent single (individual) residues may be replaced one at a time, or selected single residues may be replaced, or, in double Ala scanning, one or more pairs of two adjacent residues are both replaced by Ala. This procedure can be used to create a family of mutant proteins, each member of the family having a plurality of selected residues replaced by Ala (or by some other residue, e.g., glycine, if the wild type residue is Ala). This technique permits investigation of the impact of such point or substitution mutations on activity, function, structure, etc. of the sequence that is mutated.

Figure 10:
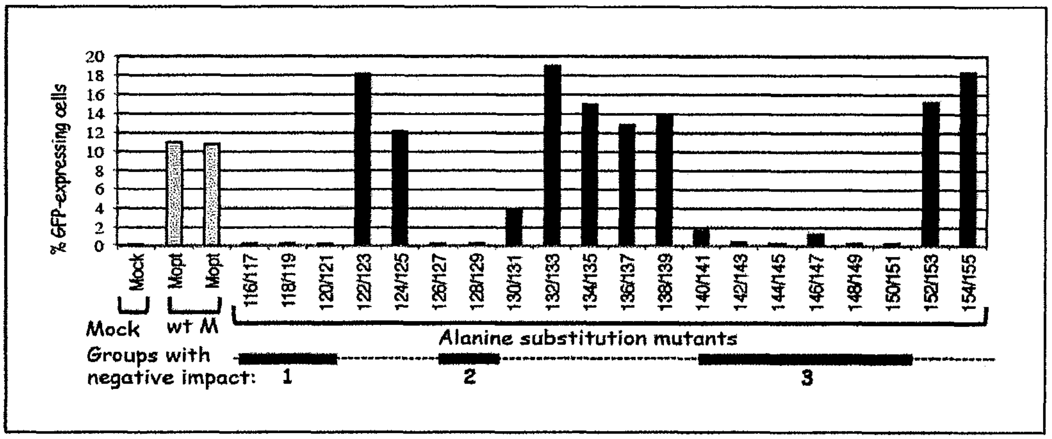
FIG. 10. Double alanine scan mutations of the region comprising residues 116-155 of M protein and impact of the M mutations on infectious virus production.

The infectivity of exemplary double alanine mutants is shown in FIG. 10 and described in detail in Example 2. Herein, such mutants are named according to the amino acid residues which were replaced, e.g., the mutant in which amino acids 122 and 123 were replaced by alanine is referred to as "mutant 122/123", etc.

The effectiveness of the vaccine composition of the invention can be evaluated by using in vitro or in vivo models. A variety of animal models of e.g., RSV infection have been described in Meignier, et al, eds., ANIMAL MODELS OF RESPIRATORY SYNCYTIAL VIRUS INFECTION (Merieux Foundation Publication, 1991). A cotton rat model of RSV infection is also described in U.S. Pat. No. 4,800,078 and Prince, et al, VIRUS RES., 3:193-206 (1985). The cotton rat model is believed to be predictive of attenuation and efficacy in humans. In addition, a primate model of RSV infection is described in Richardson, et al., J. MED. VIROL., 3:91-100 (1978) and Wright, et al., INFECT. IMMUN., 37:397-400 (1982). The complete content of each of these is herein incorporated by reference.

The present invention provides compositions/formulations for use in eliciting an immune response and/or vaccinating an individual against viruses that have a matrix (M) protein with a role/function similar to that of the M protein of RSV, namely viruses in which the M protein is essential for assembly of viable, transmissible virions. Such viruses include but are not limited to negative-strand RNA virus families such as Paramyxoviridae (for example human metapneumovirus); various parainfluenza viruses, mumps, measles, Nipah virus etc.; Orthomyxoviridae (e.g., influenza viruses such as influenza A, B and C virus; thogotovirus; and other viruses), Filoviridae (e.g., Ebola, Marburg and other viruses), Rhabdoviridae (such as rabies virus), Bornaviridae (Borna disease virus), etc. Other viruses to which an immune response may be elicited using the formulations of the invention include but are not limited to: retroviruses (which are not negative-strand RNA viruses but which have a matrix protein with similarities in function) such as lentivirus (HIV) or spumavirus (human foamy virus), or deltaretrovirus (HTLV-1), etc. Yet other exemplary viruses amenable to the present invention include, but are not limited to, those selected from Arenaviridae (e.g., arenavirus such as lymphocytic choriomeningitis virus); etc.

The antigenic compositions or formulations of the invention include one or more attenuated viruses as described herein, each of which is substantially purified and/or isolated, except that one or more of such viruses may be included in a single composition. The compositions also include a pharmacologically suitable carrier, for example a physiological compatible carrier (e.g., saline) that is compatible with maintaining the infectivity of the virus when administered (i.e., the viruses that are initially administered are capable of infecting one or more host cells), and compatible with the desired mode of administration. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of virus in the formulations may vary. However, in general, the amount in the formulations will be from about 1-99%.

In addition, the composition may contain other adjuvants. Suitable adjuvants are well known to those skilled in the art and include, without limitation, aluminum phosphate, saponins complexed to membrane protein antigens to produce immune stimulating complexes (ISCOMS), plutonic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21, and polyphosphazene, or components or derivatives thereof.

The compositions (preparations) of the present invention may be administered by any of the many suitable means which are well known to those of skill in the art, including but not limited to: by injection, inhalation, orally, intravaginally, intranasally, rectally, intradermally, by ingestion of a food or probiotic product containing the virus, topically, as eye drops, via sprays, etc. In one instance, the administration will be carried out by using an implant. In preferred embodiments, the mode of administration is by injection or inhalation. One or more than one route of administration can be employed either simultaneously or sequentially, i.e., prime boost vaccine regiments are also contemplated. Such prime boost vaccine regimens typically involve repeated vaccine administration at preselected intervals, e.g., at 1 month or 6 weeks of age then at 6 months, 1 year, and yearly thereafter, or a longer intervals, e.g., every 5 or 10 years, etc. Those of skill in the art are well acquainted with the planning, implementation and assessment of such vaccine strategies.

The vaccine compositions may be administered in conjunction with other treatment modalities. In some embodiments, such modalities may include but are not limited to various substances that boost the immune system, various chemotherapeutic agents, vitamins, anti-allergy agents, anti-inflammatory agents, etc. In other embodiments, other antigenic agents (e.g., other vaccines or vaccinogens), may advantageously administered or co-administered with the vaccines of the invention. For example, in some cases it may be desirable to combine the recombinant virus vaccine of the invention with other known vaccines which induce protective responses to other agents, particularly other childhood viruses or other infectious agents. The other vaccines may also be live attenuated virus vaccines but this need not always be the case. Such vaccines may be inactivated virus vaccines, or vaccines against other etiological agents (e.g., bacteria). This may be done by combining the vaccine agents in a single composition. Alternatively, this may be done by administering them separately but over a short time interval, e.g., at a single visit at a doctor's office or clinic, etc.

In addition, the attenuated viruses of the invention may also be further genetically engineered to contain and express genes encoding other antigens and/or agents of interest. The other agents of interest may, for example, include a foreign epitope or other "tag" or "marker" of heterologous or foreign genetic material. Such agents are useful, for example, for distinguishing between wildtype and vaccine viral strains, either in the laboratory, in nature, in a host, etc. Basically, a genetically engineered recombinant virus of the invention would carry the tag but the wildtype virus would not. This technique can also be used to distinguish between viral vaccine strains, permitting the introduction of unique genetic tags into different batches or different iterations of recombinant virus strains, to detect pirated formulations, etc. In addition, the genetically engineered viruses may contain and express detectable markers (e.g., labeling or reporter groups such as various peptides and/or proteins) e.g., for the purpose of tracing or visualizing the location of the viruses, cells infected by the viruses, or proteins translated from the viral genome; or for quantitating viruses or cells infected by virus, etc. Exemplary detectable markers include but are not limited to various fluorescent entities such as green, blue, cyan, etc. fluorescent protein (GFP) and various derivatives thereof; fluorescent proteins like dsRed, eqFP611, Dronpa, TagRFPs, KFP, EosFP, Dendra, IrisFP, etc.; and other similar molecules known in the art.

The amount of attenuated virus that is administered to a subject in need thereof varies according to many factors, e.g., the age, weight, overall health, gender, genetic history, history of allergies, prior infection or vaccine history, etc. The vaccines can be administered in a manner compatible with the dosage formulation, and in such amounts as will be therapeutically effective (e.g., immunogenic and/or protective against infection with a wild type virus). The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $10^2$ to about $10^9$ plaque forming units (PFU) or more of virus per patient, more commonly, from about $10^4$ to about $10^5$ PFU of virus per patient. The dosage may also depend, without limitation, on the route of administration, the patient's state of health and weight, and the nature of the formulation.

Upon inoculation with the vaccine composition of the invention, the immune system of the host can respond to the vaccine by producing antibodies, both secretory and serum, specific for the epitope(s) included in or expressed by the recombinant viruses. As a result of the vaccination, the host can become partially or completely immune to infection by the pathogen(s) carrying the epitope(s) or to wild type counterparts of the attenuated viruses that were injected. Where the epitope(s) is associated with HRSV, the host may become resistant to developing RSV infection, or to developing moderate or severe RSV infection, particularly of the lower respiratory tract. The immune response may be innate or adaptive, and may be either cell-mediated or humoral. Preferably, the response is adaptive and leads to immunological memory. Preferably, the response is protective, i.e., the response prevents or at least lessens the impact of (e.g., avoids development of serious symptoms of) infection by other viruses with shared antigens and/or epitopes, e.g., other Paramyxoviridae such as wild type Paramyxoviridae.

Single or multiple administrations of the vaccine composition of the invention can be carried out. In neonates and infants, multiple administrations may be required to elicit sufficient levels of immunity. Administration can begin within the first month of life, and continue at intervals throughout childhood, such as at two months, six months, one year and two years, as necessary to maintain sufficient levels of protection against the pathogen of interest. Similarly, adults who are particularly susceptible to repeated or serious infection by the pathogen of interest, such as health care workers, day care workers, the elderly, individuals with compromised immune function, and individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection.

Subjects who may be immunized using the formulations of the invention are usually mammals and are frequently humans, particularly human infants or children. However, this need not always be the case. Veterinary uses of the vaccines and methods are also contemplated, e.g., for companion pets, or for animals that are of commercial value e.g., as a food source, or for any other animal, etc.

The invention also comprises methods of eliciting an immune response to Paramyxoviridae viruses in a subject or patient in need thereof. The method includes a step of administering the pharmaceutical compositions described herein to a subject. The method may include a step of identifying suitable recipients, and/or of evaluating or monitoring the patient's reaction or response to administration of the composition. In some embodiments, the composition comprises a live, recombinant attenuated mammalian (e.g., human) RSV, and the subject is a child, and immunocompromised individual, or an elderly patient, or any patient at risk of being exposed to RSV and developing an RSV infection. The method may be a method of vaccinating such individuals against developing severe (or alternatively, moderate) lower respiratory tract disease, e.g., against developing bronchiolitis. By "child" is meant an individual who would be recognized by one of skill in the art as an infant, toddler, etc., or an individual less than about 18 years of age, usually less than about 16 years of age, usually less than about 14 years of age, or even less (e.g., from newborn to about 2-12 years of age). By "elderly" is generally meant an individual whose age is greater than about 50, usually greater than about 55, frequently greater than about 60 or more (e.g., 65 and upwards).

The recombinant virus of the invention can be used in diagnostic applications. In one embodiment, a method useful for detecting the presence or absence of an antibody specifically reactive with an epitope is provided. The method includes the steps of contacting a sample with the recombinant virus carrying the epitope, and detecting any binding between an antibody component in the sample and the recombinant virus. Suitable binding assays for this purpose include, without limitation, ELISA (enzyme-linked immunosorbent assay), RIA (radioimmunoassay), and FACS (fluorescence-activated cell sorter). This may be especially useful for embodiments in which the M protein is modified to be less active. Antibodies which specifically recognize the mutant M protein and which do not recognize a reference M protein (e.g., a control or wild type) or other different mutant M proteins may be used to detect production of the mutant M protein, either in a laboratory setting (e.g., for research purposes) and/or to monitor infections established with the attenuated virus in a subject. Antibodies which specifically recognize the attenuated viruses of the invention (both mono- and polyclonal) are also encompassed by the invention. In some embodiments, antibody recognition is selective rather than specific. Antibodies may be polyclonal or monoclonal.

The invention also encompasses cells that contain and express the live, recombinant, attenuated viruses of the invention. Such cells may be either in vitro or in vivo. One advantage of these viruses is that, due to normal or near normal levels of genome replication, the viruses will likely be easier to grow in the laboratory than are viruses in which the RNA genome is attenuated for replication. This is significant because this will allow sufficient virus to be grown to manufacture vaccine compositions. Generally, the viruses are produced in cells that are genetically engineered to contain and express a transcribeable and translatable M protein mutated as described herein, either by altering the cell genome or by introducing a genetic element (e.g., a plasmid) that encodes the mutant M. Such cells may be either constitutive or inducible, e.g., expression of M may be under control of an inducible sequence such as a tetracycline-responsive element, a temperature inducible element, an auxotrophically sensitive element inducible by complementation, or by any element that can be (usually) selectively activated or turned on and/or off, and which in turn, induces production of M. Such elements are frequently promoters or elements that interact with or are associated with promoters. Other exemplary inducible elements include but are not limited to metal inducible promoters, temperature sensitive promoters, light inducible promoters, auxotrophic cells which require complementation, etc.

In addition, in one embodiment of the invention, the inducible trigger or signal is activated by at least one transactivation element encoded by the live, attenuated recombinant viruses of the invention. In other words, the recombinant viruses themselves may be further genetically engineered to contain and express (in addition to nucleotide sequences encoding a mutant M protein) nucleic acids encoding e.g., a transactivation factor suitable for activating an inducible element in the host cell which, when activated, causes production of M protein by the host cell. An exemplary system for use in this embodiment is the Tet-responsive system, in which case the recombinant attenuated virus contains and expresses nucleic acids encoding the Tet transactivator protein. However, those of skill in the art will recognize that other similar systems exist and may also be used in the practice of this aspect of the invention, e.g., human T-lymphotropic virus (HTLV) transactivator, human immunodeficiency virus (HIV) transactivator, etc., as well as modified version thereof. In this manner, production of M is allowed in the host cell, usually in order to facilitate production of viruses, e.g., for use in preparing a vaccine, in research, etc.

Figure 11:
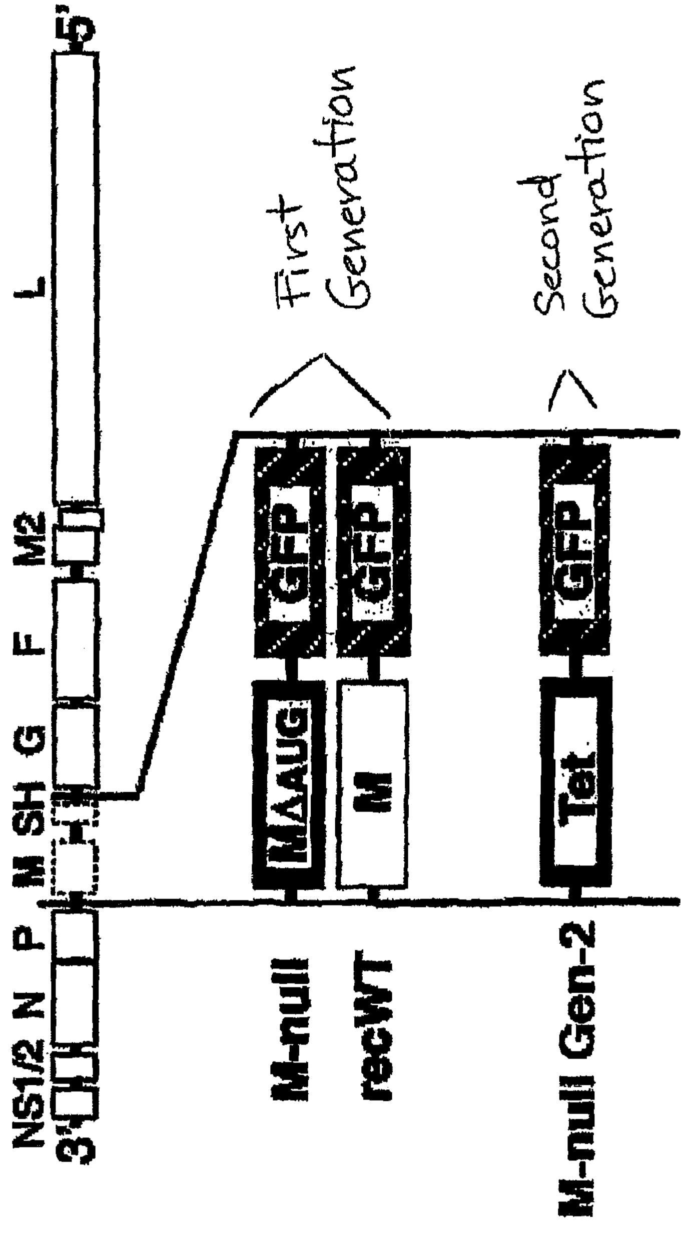
FIG. 11. Schematic comparison of compositions of first and second generations of engineered virus genomes.
Figure 12A:
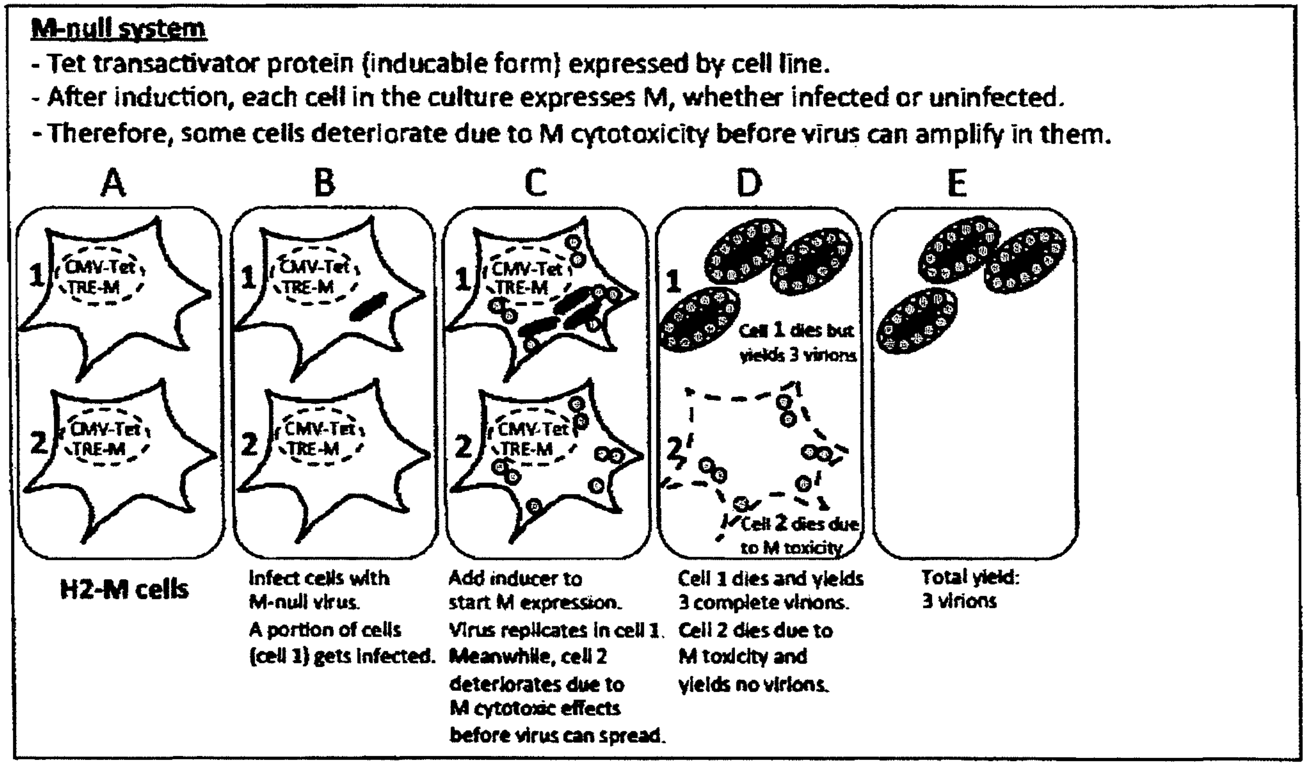
FIG. 12A-C. M-null systems. A, First generation M-null system illustrating the mechanics of virion production; B, second generation M-null system showing higher/improved yield of virions; C, M-null system with a constitutive promoter.
Figure 12B:
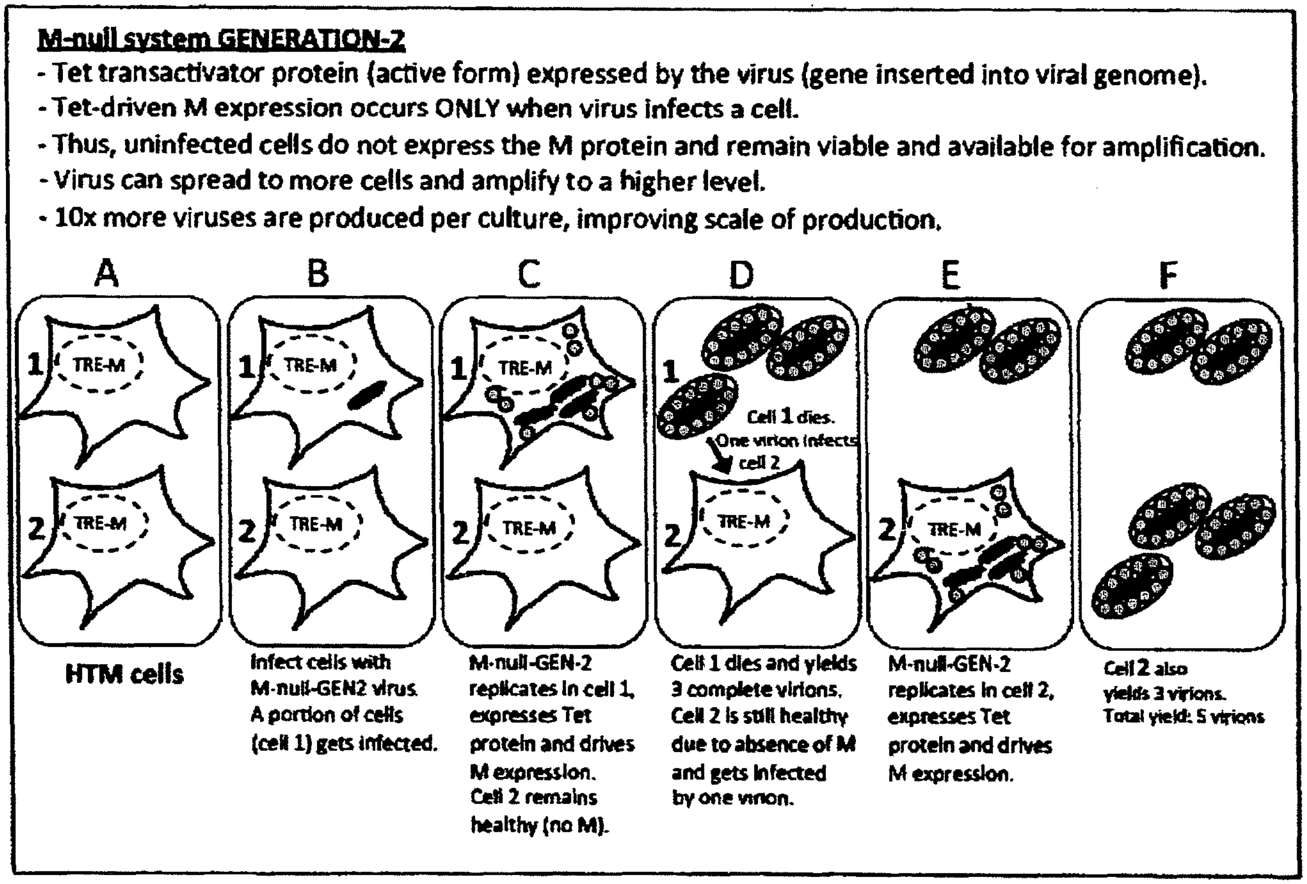

The utility of this embodiment is illustrated by FIGS. 11 and 12, in which a second generation M-null virus was produced expressing the Tet-off transactivator protein. The Tet-off transactivator protein is constitutively active and does not require doxycyclin induction. New cell lines were generated that express the M protein (M variants M122/123 or M132/133 because these were shown to better support infectious virus production, see FIG. 10) under control of the TRE element. Contrary to the H2-M line used for M-null generation-1, these new lines do not themselves express a Tet protein. This difference is shown graphically in FIG. 12: compare 12A to 12B. Thus M protein is expressed only after virus has entered a cell and expresses the Tet protein from the viral genome. The advantage of having tet expressed from the virus rather than from the cell line is that cells do not express M until virus is replicating in them and therefore remain viable for longer periods of time. This resulted in a 10-fold increase in M-null virus titer, which will benefit large scale manufacture of the M-null virus, if necessary. The tet system here utilized only serves as demonstration not as limitation. Other methods of virus-induced expression of M from a cell line can be conceived. For example, a mini-replicon expressing the M protein can be used. A mini-replicon (well known to those skilled in the art) requires the viral polymerase for replication. If the orientation of the M gene within the mini-replicon is in the anti-message-sense, no replication or M expression will occur. When the M-null virus enters a cell containing such a mini-replicon, the viral polymerase encoded by the M-null virus will jump-start mini-replicon replication and M-expression, and will theoretically result in very high levels of M protein. Expression of M from a mini-replicon within a cell line can also be achieved in a tet or otherwise -inducible fashion.

Figure 12C:
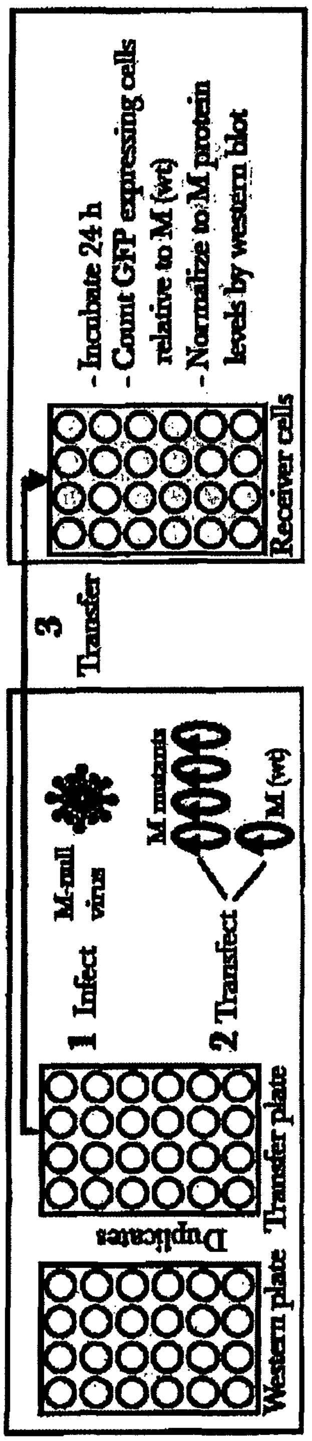

In another embodiment of the invention, a screening system for evaluating the activity, infectivity, etc., of the mutant M proteins is provided. This system, and initial results, are described in FIG. 12C and FIG. 10, and comprises the M-null virus and plasmids expressing M variants under control of a constitutive promoter, e.g., a cytomegalovirus or CMV promoter. Other exemplary promoters that may be employed include but are not limited to SV40, ubiquitin C (UBC), elongation factor-1 alpha (EF-1 alpha), phosphoglycerate kinase (PGK), CMV/chicken β-actin promoter (CAG) promoter, and others. Such a system is depicted in FIG. 12C. Whereas both generations of M-null virus can operate in this system, and the system could also be altered to included tet-inducible elements, the exemplary system shown is not inducible. In the system, regular cell types such as HEp-2 cells are infected with the M-null virus and next transfected with any one of a bank of M-variant plasmids, or a plasmid expressing wt M as a control (see FIG. 12C). The assay next measures the amount of infectious progeny produced in wells that received M-variant plasmids relative to a well that received unmodified M plasmid, by flow cytometry as indicated in the figure. If the mutant M protein is defective, viral reproduction is not facilitated and little or no infection of adjacent cells occurs. However, if the mutant M protein can provide complementary activity, then viral replication occurs, and transmission to and infection of additional cells follows. By measuring the extent of viral replication and/or infection of cells, it is possible to determine the activity or infectivity of the mutant M protein, e.g., compared to that of wild type virus. The results of M variants M116/117 to M154/155 are shown in FIG. 10, and demonstrate that M variants can be discovered that impact infectious progeny production to different levels. The purpose of this assay is to identify, in a rapid assay, M variants that can be re-inserted into the M-null viral genome, to produce M-variant viruses with specified degree of infectious progeny production and thus cell-cell dissemination.

The results of such an analysis is generally expressed in comparison to results obtained using a suitable control virus, as described elsewhere herein. Generally, levels of infection progeny production within less than about 5%, or 10%, of that of a comparable control are considered to not be statistically significant (e.g., when analyzed using Student's t-test). However, results which show viral production that is less than about 90% of that of the control are considered to be indicative of "decreased" or lessened production. In some embodiments, decreased levels of viral production are about 80, 75, 70, 65, 60, 55, 50, 45, 40, 35, 30, 25, 20, 15, 10, 5, or even 0% of that of the control. In contrast, "increased" levels are those which are at least about 15, 20, 25, 30, 35, 40, 45, 50, 55, 60, 65, 70, 75, 80, 85, 90, or 100% (i.e., 2 fold) higher, or even more, e.g., 2, 3, 4, 5, or more fold higher, than a control. These values represent threshold values for determining whether a mutant M protein causes and increase or decrease (or no change) in viral infectivity.

The results of the screening method shown in FIG. 10 also identify M mutations that increase rather than decrease the level of infectious virus progeny (mutants 122/123, 132/133, 152/153, and 154/155). Although such mutants do not have utility for generation of live-attenuated viruses, they may have important advantages in the production of virus-like particles (VLPs), for which the M protein forms the basis. VLPs are another safe alternative to vaccination as they lack the viral genome. VLPs are made by adding selected viral proteins to the M protein in transfected cell cultures—the M protein thus forms the basis of VLPs. Although the ability of VLPs to induce a protective immune response in humans has not been demonstrated, they are attractive vaccine alternatives under conditions whereby patients may have a compromised immune system. Difficulties in the production of VLPs have been reported, which are associated with insufficient yield. As M proteins that improve infectious progeny yield are discovered, these mutants are likely to also increase the yield of VLP production. Moreover, the screening system described in the paragraph above allows screening for additional M variants that may further benefit VLP production. Thus, the screening system represents a novel method to discover M variants that will help overcome difficulties in VLP production.

Exemplary mutants include but are not limited to, with reference to FIG. 10, double alanine mutants 122/123, 124/125, 132/133, 134/135, 136/137, 138/139, 152/153, and 154/155, each of which display activity greater than that of the wt virus. The naming convention employed herein for such mutants is described above.

It should be understood that the above-described embodiments and the following examples are given by way of illustration, not limitation. Various changes and modifications within the scope of the invention will become apparent to those skilled in the art from the present description.

EXAMPLES

Example 1. The Human Respiratory Syncytial Virus Matrix Protein is Required for the Formation and Maturation of Virus-Induced Filaments Abstract An experimental system was developed to generate infectious human respiratory syncytial virus (HRSV) lacking matrix (M) protein expression (M-null) from cDNA. The role of the M protein in virus assembly was then examined by infecting HEp-2 and Vero cells with the M-null virus, and assessing the impact on infectious virus production and viral protein trafficking. In the absence of M, infectious progeny production was strongly impaired. Immunofluorescence (IF) microscopy analysis using antibodies against nucleoprotein (N), attachment protein (G), and fusion protein (F) failed to detect the characteristic virus-induced cell surface filaments, which are believed to represent infectious virions. In addition, a larger proportion of the N protein was detected in viral replication factories termed inclusion bodies (IBs). High resolution analysis of the surface of M-null virus infected cells by field emission scanning electron microscopy (SEM) revealed the presence of large areas with densely packed, uniformly short, filaments. Though unusually short, these filaments were otherwise similar to those induced by an M-containing control virus, including presence of the viral G and F proteins. The abundance of the short, stunted, filaments in the absence of M indicates that M is not required for the initial stages of filament formation but plays an important role in the maturation or elongation of these structures. In addition, the absence of mature viral filaments and simultaneous increase of N protein within IBs suggest that the M protein is involved in transport of viral ribonucleoprotein (RNP) complexes from cytoplasmic IBs to sites of budding.

Introduction

HRSV is an important viral agent of respiratory tract disease in infants, children, immunosuppressed individuals, and the elderly (15, 24, 48). In absence of a vaccine, prevention and treatment of HRSV disease remain a significant challenge. HRSV is a single-stranded negative-sense RNA virus of the family Paramyxoviridae. Its genome expresses 11 known proteins, among which are three transmembrane glycoproteins (small hydrophobic protein (SH), G, and F), and the viral M protein (14, 28). G is a highly glycosylated protein that is expressed as a secreted and a membrane-anchored form, the latter serving as a viral attachment protein (34). F resembles the prototypic paramyxovirus fusion protein but can induce membrane fusion in the absence of G (26, 39). F also appears to play a role in viral attachment, and nucleolin was recently identified as a cellular receptor for the F protein (57). M is a non-glycosylated phosphorylated protein of 256 amino acids, and a structural component of the HRSV virion (19, 27, 52). M is thought, in part by analogy to the role of matrix proteins in other virus systems, to play a key role in virion assembly by inhibiting viral transcription and by forming a bridge between the viral RNP and envelope (13, 21, 25, 27, 54, 56). However, the roles of HRSV M in virion assembly have not been well characterized. A better understanding of the mechanisms underlying assembly has the potential to improve yield and purity of HRSV stocks for large-scale production and worldwide distribution of future vaccines, to help predict the potential for cell-cell transmission (and safety) of live vaccine candidates, and to lay the groundwork for the use of virus-like particles (VLP) as an alternative vaccine strategy.

HRSV infectivity is predominantly associated with a filamentous form (1, 22, 41, 51, 60). These viral filaments are produced at the cell surface late in the infection cycle and remain largely attached to the infected cells, where they can be readily visualized by IF or electron microscopy (EM). Viral filaments range in lengths from 2 to 8 μm, contain high concentrations of N, G and F proteins, and often appear as aggregates (1, 16, 31, 43, 51, 53, 55). In a study where anti-RhoA drugs were used to block the formation of viral filaments, virion morphology was reported to shift from predominantly filamentous to predominantly round, without affecting the total yield of infectivity (22). This would suggest that while the filamentous phenotype is perhaps the 'preferred' morphology, the virus has significant potential to generate infectious virions of non-filamentous morphology.

Recent studies using viral genomic RNA (vRNA) visualization, transmission EM (TEM) tomography, and proteomic analysis of purified viral filaments suggest that the filaments contain multiple viral RNPs (49, 53). How the RNPs are recruited to budding sites and incorporated in viral filaments is not known. HRSV RNPs are believed to be synthesized in virus-induced IBs. IBs form in the cytoplasm relatively early in the infection cycle, and contain all the components of the viral polymerase complex (N, phosphoprotein P, catalytic polymerase subunit L, processivity factor M2-1), M, and cellular proteins, many of which are also found in purified viral filaments (17, 49). TEM studies have reported that IBs and sites where viral filaments form are sometimes in close proximity (30, 49), suggesting that IBs may be the scaffold from which viral filaments are generated. However, the composition and functions of IBs, including a potential role in viral filament formation, are poorly understood. Several reports have implicated cytoskeletetal elements in the processes that lead to virus egress, in particular microtubules, myosin V, actin, and actin-regulatory proteins such as profilin and RhoA (30, 32, 59). In addition, a role for an actin/myosin-based motility system in HRSV exit has been proposed (6, 53, 59), and there is strong evidence for the involvement of lipid rafts (8, 9, 22, 27, 31, 36, 49, 50, 53).

Studies with other paramyxoviruses have shown that their M proteins play a role in the assembly of virus particles (12, 29, 40, 46). A requirement for HRSV M in cell culture propagation was previously reported, based on an HRSV minireplicon system (58). Studies of host cell infection by HRSV in the absence of the SH, G, and F proteins point to M as an important determinant of virion release (2, 3). The roles of M in the viral assembly process likely include a function in bringing together the RNP and viral envelope, since an M-containing sheath was revealed when the lipid membrane was removed from HRSV induced surface filaments (1, 27). In HRSV infected cells, the M protein is first detected in the cytoplasm and nucleus (19). The purpose of nuclear targeting is not well understood but may serve to inhibit host cell transcription or to temporarily divert M away from sites of viral transcription which it was shown to inhibit (18, 21). At later times M is increasingly detected in virus-induced IBs (18, 21, 35). M was shown to associate with viral RNPs through interaction with the M2-1 protein, and also has RNA-binding capacity (35, 52). M binds both plasma and internal cellular membranes, and was reported to interact with the G protein cytoplasmic tail (CT) (20, 27). Several of these observations agree with a predicted role for M in the late stages of virion production. In carrying out this role, HRSV M appears unique in that known viral Late domains have not been identified and budding was found to be independent of ubiquitination and vacuolar protein sorting-associated protein 4 (13, 60). Another unique characteristic of the HRSV M protein is its structural relatedness to the Ebola virus matrix protein VP40 (33, 38).

To characterize the roles of HRSV M in the late stages of the infection cycle, an infectious M-null virus was generated and progeny virus production and viral protein distribution in the absence of M was analized. The 'null' virus approach was pursued chiefly because of the possible downstream advantages for the study of the role of M, such as the generation of engineered viruses with debilitating M mutations. The results of this study present novel insights into the process of viral filament formation, and provide a platform from which to further dissect the role of M in the viral life cycle.

Materials and Methods

Cells and Primary Antibodies.

Vero and HEp-2 cells were acquired from the American Type Culture Collection and grown in standard growth medium containing 5% FBS. Monoclonal antibodies L9 (anti-G) and A5 (anti-F) were provided by Edward Walsh (University of Rochester School of Medicine, Rochester, N.Y.). Synagis (anti-F) and anti-N antibodies were acquired from MedImmune, Inc. and AbD Serotec respectively. A rabbit polyclonal anti-M peptide serum (M residues 18-31) was produced and affinity purified by Genscript.

Construction of a Codon-Optimized M ORF.

The M ORF of the HRSV A2 strain was codon optimized according to Haas et al (23). Overlapping oligonucleotides (70 nucleotides with 22 nucleotide overlap, Operon Biotechnologies), representing the entire codon-optimized ORF, were assembled and PCR-amplified with flanking BsrGI and XhoI restriction sites. The product was cloned using BsrGI and XhoI restriction sites into a pcDNA3-derived plasmid (modified to lack the T7 promoter and the neomycin gene cassette, and to contain an additional BsrGI restriction site). The codon-optimized M ORF was sequence verified. Errors due to the use of long primers were corrected using site-directed mutagenesis and the final plasmid was named pc-Mopt.

Generation of an Inducible M-Expressing Cell Line.

The codon-optimized M ORF was PCR amplified with flanking EcoRI and XbaI sites, and cloned into pTRE-Tight (Clontech). The resulting plasmid (pTRE-Mopt), was used to generate an inducible M-expressing HEp-2-derived cell line in two steps. First, HEp-2 cells were transfected with plasmid pTet-on-Advanced (Clontech), and G418-resistant colonies were identified and amplified in G418-containing medium. Resistant colonies were screened by transfecting with a plasmid expressing enhanced green fluorescent protein (EGFP) from a tet-inducible promoter (pTRE-EGFP), and incubating transfected cells in the presence of doxycyclin (DOX). A cell line with strong induction, as well as low EGFP expression in the absence of DOX, was subcloned twice by limiting dilution, and named H2-tet. Second, plasmid pTRE-Mopt, along with linearized hygromycin gene (Clontech), was transfected into H2-tet cells, and G418/hygromycin-resistant colonies were selected. Resistant colonies were amplified and screened for their level of M expression by adding DOX to the medium, fixing cells 24 h after addition, and staining with anti-M serum followed by goat-anti-rabbit antibodies carrying alexa-488. A colony with high level of inducible M expression was identified with a fluorescence microscope and subjected to another round of subcloning by limiting dilution, and named H2-M.

Western Blot Analysis.

Equivalent cell numbers (~6,000 cells per lane) of each sample were electrophoresed on reducing 12% SDS-PAGE gels, and a western blot was generated. The blot was incubated with anti-M peptide serum followed by goat-anti-mouse antibodies conjugated to horseradish peroxidase, and developed using ECL (Pierce).

Construction of M-Null and recWT cDNAs.

In previous work, a cDNA (A2 strain) was generated in which the SH ORF was replaced with that of EGFP (pRSΔSH)(43). Virus recovered from cDNA pRSΔSH (which contained artificial restriction sites to facilitate glycoprotein gene exchange) replicated to levels indistinguishable from those of an unaltered A2 virus, and EGFP expression from this location was shown to be an accurate indicator of infectivity correlating with the number of plaque forming units (PFU) (10, 43, 44). For this project another cDNA was constructed that also had an exact replacement of the SH ORF with that of EGFP but did not contain artificial restriction sites. This cDNA was designated pRSV-ΔSH/GFP (see FIG. 2A, 'recWT'). From pRSV-ΔSH/GFP, a cDNA was constructed that lacks the M ORF and contains instead a linker region with BsmBI restriction sites (pRSV-ΔSH/GFP-ΔM/Bsm). Next, seven of the eight methionine codons in the authentic M ORF were mutated (methionine 1 to AAC; methionines 2-7 to UAA). Methionine eight is located near the COOH-terminal end of the ORF and was left intact. The mutated M ORF was designated 'MΔAUG'. The 'MΔAUG' ORF was PCR-amplified with flanking BsmBI sites, such that after ligating the product into pRSV-ΔSH/GFP-ΔM/Bsm following BsmBI digestion, no artificial sequences were retained other than the intended AUG mutations of the M ORF and the exact replacement of the SH ORF with that of eEGFP (see FIG. 2A, 'M-null'). The M-mutated cDNA was designated 'pRSV-M-null'.

Recovery of Infectious Virus from cDNA.

Infectious virus was recovered from cDNAs pRSV-M-null and pRSV-ΔSH/GFP as previously described (45), with the following modifications (for cDNA pRSV-ΔSH/GFP, only modification 1 and 2 apply): 1) Initial transfection of the cDNA and support plasmids was done in BHK-21 cells expressing T7 polymerase from a nonpathogenic alphavirus replicon (47); 2) the N, P, M2-1, and L support plasmids contained an IRES preceding the ORF; 3) pc-Mopt plasmid was included in the initial transfection to ensure virion production; 4) infectious virus was amplified in H2-M cells. Viral RNA was harvested from cells infected with the recovered viruses (passage 3 for recWT and passage 5 for M-null virus) and amplified by reverse-transcription PCR. Modified areas (M and EGFP genes and surrounding intergenic regions) plus the N, G, and F genes were verified by bulk nucleotide sequence analysis. No unintended nt changes were found. Passage 3 stocks of recWT virus, and passage 5 and 6 stocks of M-null virus were used for the experiments described.

Cell ELISA.

Relative protein expression levels were determined by cell ELISA as previously described (42, 44), with minor modifications. Briefly, infected cells were fixed at 26 hpi and permeabilized with 0.2% triton (for N, G, F) or 0.1% SDS (for M). Fixed, permeabilized cells were blocked and labeled with anti N, M, G, or F (A5) antibodies followed by hrp-conjugated secondary antibodies (anti-mouse for N, G, F antibodies, anti-rabbit for M antibody (Pierce)). After washing, cells were incubated in O-phenylenediamine-based substrate solution. At short time intervals after addition of substrate, small aliquots were collected and immediately added to 3M sulfuric acid to stop the reaction. OD490 was determined in an ELISA plate reader. The experiment was carried out in triplicate, yielding similar relative protein expression levels. Due to significant overall variation in ELISA signal strengths between replicate experiments, a single result of three independent experiments is shown.

Growth Analysis (Flow Cytometry).

HEp-2 cells plated in six-well plates were infected by adding inoculum (~0.2 PFU/cell) and centrifugation at 3,000×g for 10 min (Beckman Coulter, Allegra X-15R) to boost the infection rate. Total (cell-associated and released) progeny virus was harvested immediately after infection and at 1 day intervals thereafter, by scraping cells into the medium and storing at −80° C. Samples were assayed simultaneously by flow cytometry as previously described (43). Briefly, samples (20% of the total volume harvested) were thawed, mixed by gentle pipetting, cleared by low speed centrifugation (5 min, 750×g), and used to infect freshly plated (receiver) HEp-2 cells. At 24 hpi, receiver cells were trypsinized, fixed with 4% paraformaldehyde in suspension, and the percentage of GFP-expressing cells was determined by flow cytometry, counting 50,000 cells per sample.

IF Microscopy.

Figure 1B:
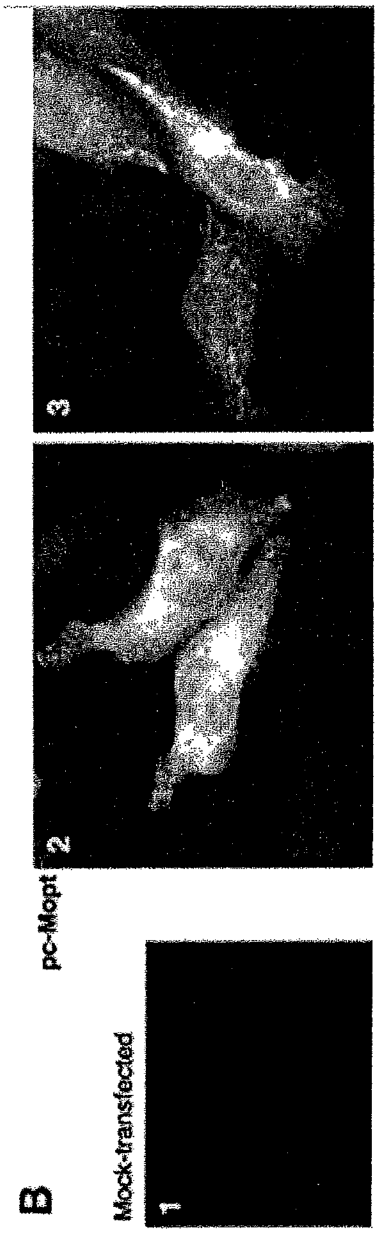

Cells were fixed with freshly dissolved 4% paraformaldehyde, permeabilized with 0.1% SDS, and incubated with anti-M peptide serum. Following incubation with alexa-488 conjugated anti-rabbit antibodies, cells were stained with DAPI, washed, and photographed at 200× magnification on a Nikon inverted fluorescence microscope (FIG. 1C), or washed, mounted on slides, and photographed at 600× magnification (FIG. 1B). To examine GFP expression within infected cells (FIG. 3B), cells were photographed at 100× magnification without fixation or processing, using UV light to visualize GFP or halogen light for phase-contrast images.

Confocal Microscopy.

Vero cells on glass coverslips were infected for 1.5 h at 37 C (~0.2 PFU/ml). At 26 hpi, cells were fixed and processed for confocal microscopy as previously described (43), using L9 (G) and A5 (F) as primary antibodies and anti-mouse secondary antibodies conjugated to alexa-594. Cells were photographed using a Leica TCS SP2 inverted confocal microscope system using a 63× objective and ~3.5× zoom.

Field Emission SEM.

HEp-2 cells on plastic coverslips were infected as described under 'Growth analysis'. At 26 hpi, the medium was replaced with MEM reduced serum medium (MEM-RS, Hyclone) containing anti-G (L9) and anti-F (Synagis) antibodies, 50 mM Hepes, and 0.1% BSA, and cells were incubated for 1 h at room temperature. 1 mM sodium azide was added to the medium 30 min prior to antibody incubation, and during primary antibody incubation, as a precaution to avoid internalization of antibodies. Inclusion of sodium azide had no measurable impact on the appearance of surface filaments on the surface of recWT infected cells (not shown). Cells were washed twice and incubated with goat-anti-mouse or goat-anti-human antibodies (conjugated to 15 nm and 25 nm colloidal gold respectively; Aurion) in MEM-RS containing 0.1% BSA for 1 h on ice. Cells were washed three times and fixed in 2.5% glutaraldehyde for 30 min at room temperature. After fixation, cells were washed once, incubated in 1% osmium tetroxide for 1 h, and washed three additional times. Cells were then dehydrated in ethanol in stepwise fashion, and incubated in hexamethyldisilazane for 1 min. Following hexamethyldisilazane treatment, samples were air-dried, carbon-coated, and examined in an FEI Quanta 600 field-emission gun scanning electron microscope. Samples were examined using secondary electron (SE) and backscattered electron (BSE) modes at various magnifications, and photographed at 20,000 and 100,000×. Of each sample, approximately 25 fields containing infected cells (identified by the presence of anti-G and -F conjugated gold particles) were examined. No gold particles were found in the uninfected cell sample. Images at 100,000× were overlaid to determine the location of gold particles relative to identified surface filaments.

Results

Transient and Stable Expression of the M Protein from a Codon-Optimized ORF.

Due to the generally low levels of nuclear promoter-driven expression of HRSV proteins, a synthetic, codon-optimized M ORF was assembled from oligonucleotides and cloned into a pcDNA3-derived vector (pc-Mopt). To examine transient M expression from plasmid pc-Mopt, HEp-2 cells were transfected and processed for IF microscopy and western blot analysis (FIG. 1). For the latter, transfected cells were harvested 30 hours after start of transfection (hpx), and subjected to SDS-PAGE under reducing conditions. As a negative and positive control for M expression, lysates from an equal number of mock-transfected HEp-2 cells and cells infected with wt HRSV were included. The M protein was detected using an anti-M peptide serum (see "Materials and Methods" above). In lysates of pc-Mopt transfected cells (FIG. 1, lane 3) and wt HRSV infected cells (FIG. 1, lane 1), anti-M antibodies identified a protein of 27 to 28 kD, consistent with previous reports (19, 52). No obvious difference in molecular weight was observed between M expressed alone or in the context of a viral infection. For IF microscopy, pc-Mopt transfected cells were fixed at 30 hpx, permeabilized with 0.1% SDS, and incubated with anti-M serum followed by alexa-488-conjugated secondary antibodies. Consistent with the western blot results, the M protein was abundantly expressed in pc-Mopt (FIG. 1B, panels 2 and 3) but not in mock-transfected (FIG. 1B, panel 1) cells. In most cells examined, M was present throughout the cytoplasm (FIG. 1B, panel 2). Sometimes, M appeared to concentrate in cell structures near the plasma membrane (FIG. 1B, panel 3). M was also routinely detected in the nucleus (FIG. 1B, panel 2), in agreement with previous observations in virus-infected cells (17). At late times post transfection, M expression resulted in a high rate of cell rounding and detachment.

Figure 1C:
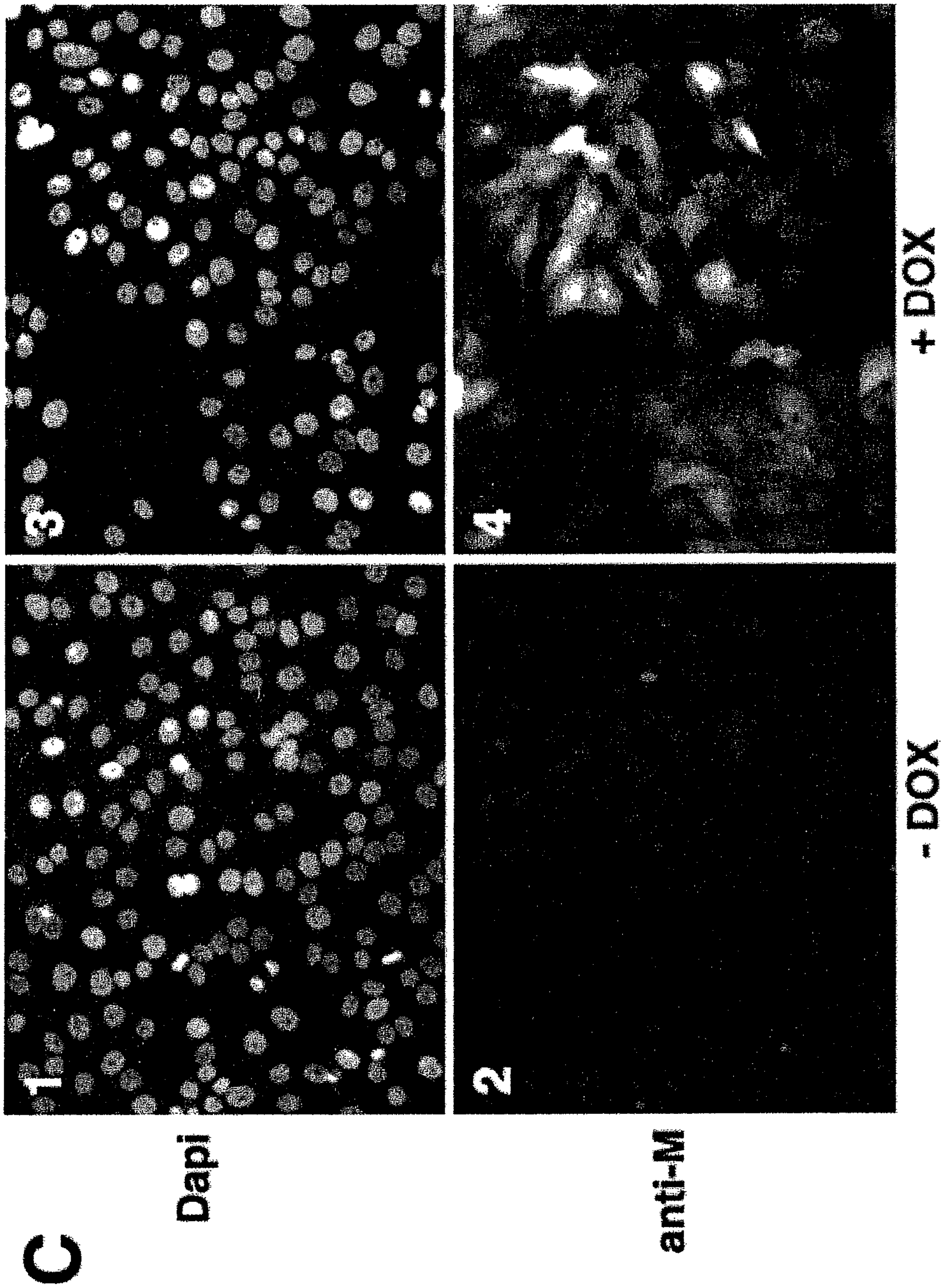

To avoid cytotoxic effects of constitutive expression, the Mopt ORF was cloned behind a tet-inducible promoter (pTRE-Mopt), and an inducible M-expressing cell line was generated as described in Materials and Methods, and named H2-M. FIG. 1C documents M expression by cell line H2-M in the presence (panels 3 and 4) or absence (panels 1 and 2) of DOX inducer, 30 hours post induction. DOX-induced H2-M cells were also examined by western blot (FIG. 1A, lane 5) with equivalent cell numbers loaded per lane. H2-M cells expressed a peptide of the correct molecular weight albeit at a level lower than that of virus-infected or transiently transfected cells.

Generation of an M-Null Virus Using Trans-Complementing Cell Line H2-M.

Figure 2A:
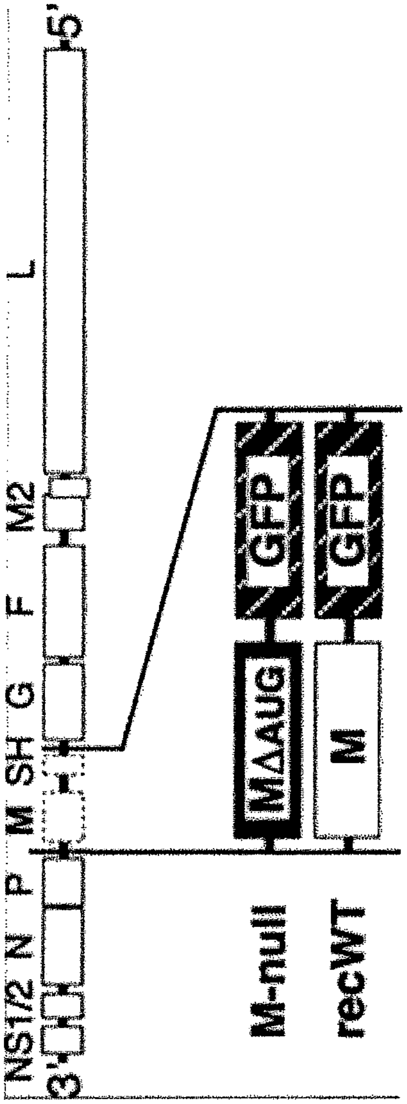
FIGS. 2A and B. Composition of engineered virus genomes and viral protein expression. (A) Genome content of engineered viruses. In virus 'M-null', the M ORF was replaced with a modified M ORF in which AUGs were mutated to ablate expression, and the SH ORF was replaced with the EGFP ORF for tracking purposes. (A virus having the SH ORF replaced with that of EGFP was previously shown to replicate in a manner indistinguishable from wt virus (10, 43, 44)). The properties of M-null virus were compared to control virus 'recWT'. recWT virus also has a replacement of the SH ORF with that of EGFP, but contains an unaltered (wt) M ORF. Virus recWT resembles the previously reported virus RSΔSH (43), but is a second generation virus in which all artificial restriction sites were removed. (B) Viral protein expression by cell ELISA. HEp-2 cells were infected with virus M-null or recWT, or left uninfected as a control, and were fixed and permeabilized at 26 hpi. Relative protein levels were measured with anti-N, M, G, and F antibodies by cell ELISA as previously described (42, 44). OD490: optical density at 490 nm. A representative result of several independent experiments is shown.

The HRSV A2 strain M protein contains eight methionines. Seven of these occur within the approximate amino-terminal half of the ORF, and were mutated to ablate expression (MΔAUG). A cDNA was also generated in which the M ORF was replaced with a spacer containing remote-cutting BsmBI restriction sites (see Materials and Methods). In this cDNA, the SH ORF was replaced with that of EGFP, to allow monitoring of infectious virus recovery and cell-to-cell spread. SH was previously shown to be dispensable for virus replication in cell culture, and EGFP expression from the SH location was shown to be an accurate and stable indicator of infectivity correlating with the number of PFU (10, 43, 44). While previous studies do not suggest a major role for the SH protein in viral assembly (2, 3, 42, 43, 44, 58), the reader should keep in mind that these studies were carried out in its absence. The resulting cDNA was named pRSV-ΔM/Bsm-ΔSH/GFP. Next, the MΔAUG ORF was PCR-amplified using primers to incorporate flanking BsmBI sites, and ligated into BsmBI-digested pRSV-ΔM/Bsm-ΔSH/GFP cDNA, such that no artificial sequences were remaining anywhere in the cDNA other than the intended M mutations and an exact replacement of the SH ORF with that of EGFP. The gene content of the resulting cDNA ('M-null') is shown in FIG. 2A. A cDNA also having EGFP in place of SH but containing the unaltered M ORF, was constructed to serve as a control ('recWT; FIG. 2A). Note that the 'recWT' cDNA is a subsequent generation cDNA having SH replaced with EGFP, engineered such that artificial restriction sites (to facilitate glycoprotein exchange) contained within the 2003 version (43) are no longer present.

Infectious virus was recovered from the above cDNAs as previously described (44), see Materials and Methods. Recovery of the M-null virus required inclusion of plasmid pc-Mopt in the initial transfection and the use of H2-M cells. While M-containing virus (designated 'recWT') amplified to relatively high titer in two passages in HEp-2 cells, M-lacking virus (designated 'M-null') required four passages in H2-M cells to obtain a titer of $1\times10^5$ PFU/ml. Virus stocks used for the experiments described were verified by reverse-transcription PCR on RNA harvested from infected cells at passage 5 (M-null) or passage 3 (recWT), followed by sequence analysis as previously described (44). No unintended changes were found (data not shown).

Characterization of Protein Expression by the M-Null Virus.

Figure 2B:
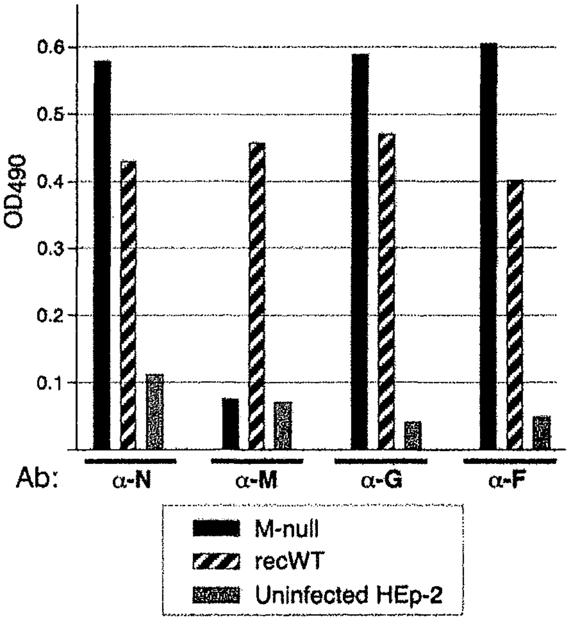

To examine protein expression by the recovered viruses, HEp-2 cells were infected with M-null virus or M-expressing control virus recWT, and examined at 26 hpi by cell ELISA as previously described (45) (FIG. 2B). The results consistently demonstrated both the lack of M expression in M-null virus infected cells and moderately higher levels of N, G, and F proteins in the absence of M. A representative result of several independent experiments is shown in FIG. 2B. Viral protein expression was also verified with IF microscopy (data not shown). The results of cell ELISA and IF microscopy analyses were in agreement with the gene content indicated in FIG. 2A.

The M Protein is Required for Cell-Cell Transmission of HRSV.

Using a minireplicon system, it was previously shown that the M protein is required for virus transmission (58). However, this study was done in the context of vaccinia and wt HRSV helper virus, and examined only virus released to the supernatant, which typically constitutes a minority of total HRSV infectivity. To ask whether HRSV cell-to-cell transmission, be it through released virions or by alternate mechanisms, can occur in the absence of M, HEp-2 cells were infected with M-null or recWT virus (0.2 PFU/cell), and progeny virus harvested at day 0 and at 1 day intervals thereafter. Total (cell-associated and released) virus was assayed by flow cytometry as previously described (43). Briefly, clarified lysates of infected cells were used to infect receiver HEp-2 cells. At 24 hpi, receiver cells were trypsinized and fixed, and the percentage of GFP-expressing cells was counted to determine the relative amount of progeny virus present at each timepoint (FIG. 3A). As expected, recWT virus produced a significant amount of progeny virus by day 1 post-infection. By day 2, sufficient recWT progeny virus was produced to infect the majority (>70%) of receiver cells. In contrast, infectious progeny virus production in the absence of M was very low, with less than <0.01% of receiver HEp-2 cells expressing GFP at day 2, 3, and 4. Propagation of the viruses was also examined by monitoring GFP-expressing cells within the infected culture at daily intervals (FIG. 3B). In agreement with the flow cytometry results, cells infected with control virus recWT spread to neighboring cells at a high rate, and by day 3, the majority of cells were expressing GFP (FIG. 3B, bottom panels). Cells infected with the M-null virus also displayed high levels of GFP expression, but virus failed to spread and invade the culture (FIG. 3B, top panels). In many cases small, strongly fluorescent, multinucleated syncytia formed at sites where individual cells were initially infected. However, M-null virus did not spread beyond the observed syncytia, even after several days post-infection, and uninfected cells continued to divide rapidly for the duration of the experiment (FIG. 3B, Day 4 (phase)). Taken together, these results demonstrate that the M protein was critical for virus propagation in cell culture. However, the F protein remained fusion-competent in the absence of M, and induced a moderate amount of virus spreading via syncytium formation.

Distribution of Viral Proteins is Altered in the Absence of M.

Figure 4:
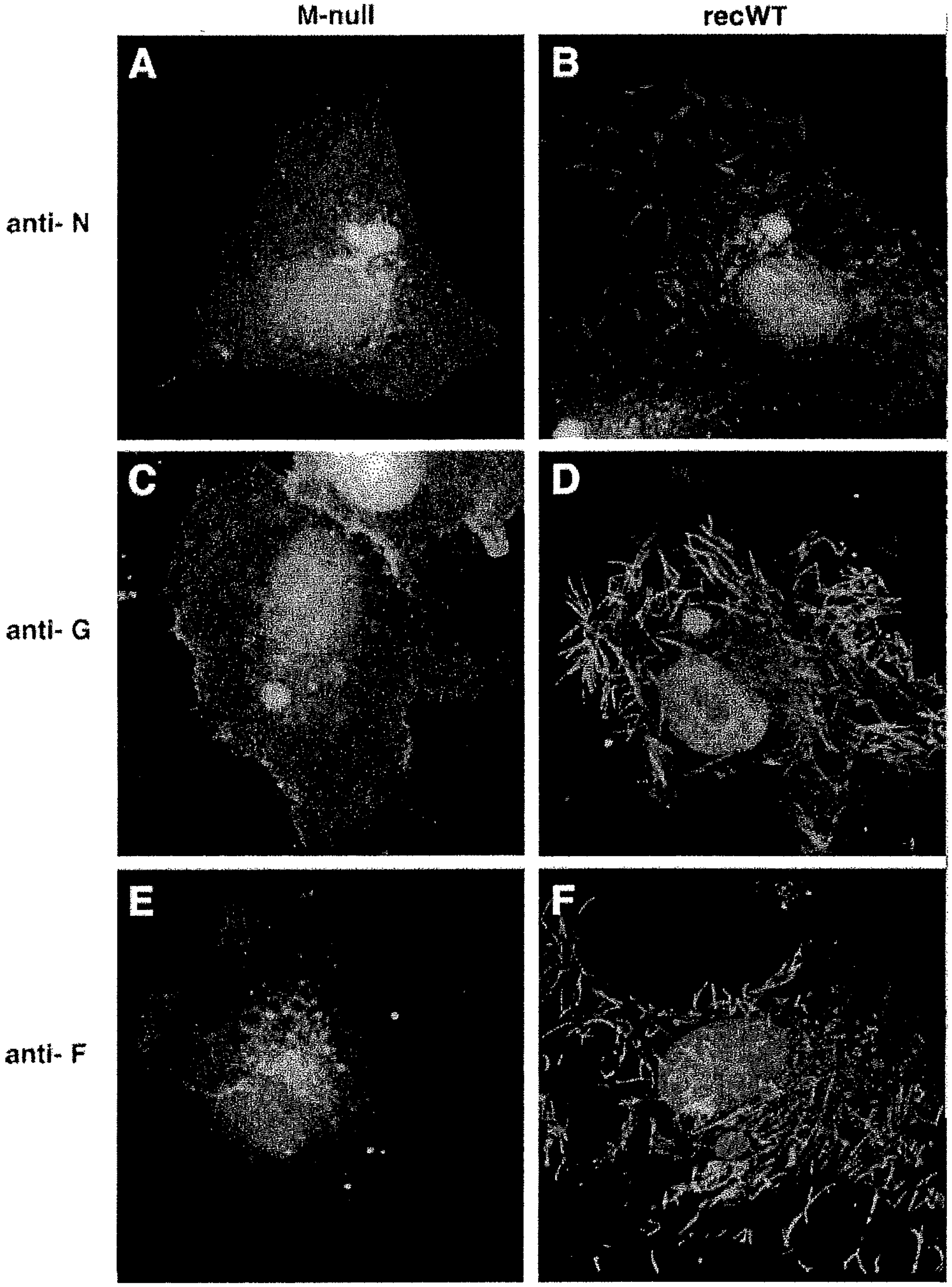
FIG. 4. Subcellular distribution of the N, G, and F proteins in infected cells in the absence of M. Vero cells infected with recWT (panels B, D, F) or M-null virus (panels A, C, E) were fixed at 26 hpi and detergent-permeabilized. Samples were incubated with anti-N (panels A, B), anti-G (panels C, D) or anti-F (panels E, F) antibodies. Following incubation with alexa-594-conjugated secondary antibodies, samples were examined on a confocal microscope by scanning sequentially for GFP expression (green) and N, G, or F expression (red). Images were overlaid. Magnification: approximately ×2,000.

M is thought to facilitate virion assembly by bringing together the RNP and envelope glycoproteins. In this experiment, the impact of M absence on subcellular targeting of the N, G and F proteins was examined using IF microscopy (FIG. 4). This was done in Vero cells since they attach more readily to glass coverslips. Cells were infected with the M-null or recWT virus, fixed and permeabilized at 26 hpi, and incubated with anti-N, anti-G, or anti-F antibodies. Following incubation with alexa-594 conjugated secondary antibodies, cells were examined by confocal microscopy. In both M-null and recWT infected cells, GFP expression was abundant, indicating successful infection and viral replication (FIG. 4, all panels). In recWT infected cells, the typical distribution pattern for the N protein was observed: N was concentrated in cytoplasmic IBs and in viral filaments located at or near the cell surface, and was also present diffusely in the cytoplasm (FIG. 4, panel B). In addition, N was abundantly present in long filaments extending far from the cell surface. However, these long filaments were thin relative to filaments labeled with G or F antibodies and difficult to capture with photography. The latter may be due to the location of N inside the virion structure. In M-null virus infected cells, expression of N protein was substantially different: while high levels of N were also observed in the cytoplasm, viral filaments were not detected, and the amount of N protein present within IBs appeared to have increased (FIG. 4, panel A). To quantitate the observed increase, ten random fields were chosen in M-null and recWT infected cells, photographed, and the number and area of N-labeled IBs were measured using Nikon NIS Elements software. It was found that in the absence of M, the number of IBs was unchanged, but the average area occupied per IB had increased by approximately 2-fold (data not shown). Thus, the lack of M expression led to an increase of N protein in IBs and a notable absence of N-containing viral filaments.

In Vero cells infected with recWT virus, the G and F proteins also concentrated in viral surface filaments (FIG. 4, panels D and F). In contrast, in the absence of M, viral filaments were not detected using anti-G and -F antibodies. Rather G and F were found at the plasma membrane in an evenly distributed though punctate manner (FIG. 4, panels C and E). In addition, round structures resembling IBs were often observed near the plasma membrane of M-null virus infected cells labeled with anti-F antibody (FIG. 4, panel E). Surface expression of F and G in infected cells was verified in duplicate, non-permeabilized, samples (data not shown). Combined with the N protein data shown above, it appeared that absence of M precluded the formation of cell surface filaments. Whereas F protein subcellular targeting appeared to be altered, significant amounts could still be detected at the cell surface. The altered distribution of the N, G, and F proteins in the absence of M was also observed in HEp-2 cells (not shown), indicating that the results were not a cell type-dependent phenomenon.

Virus-Induced Cell Surface Filaments are Stunted in Absence of M.

Figure 5:
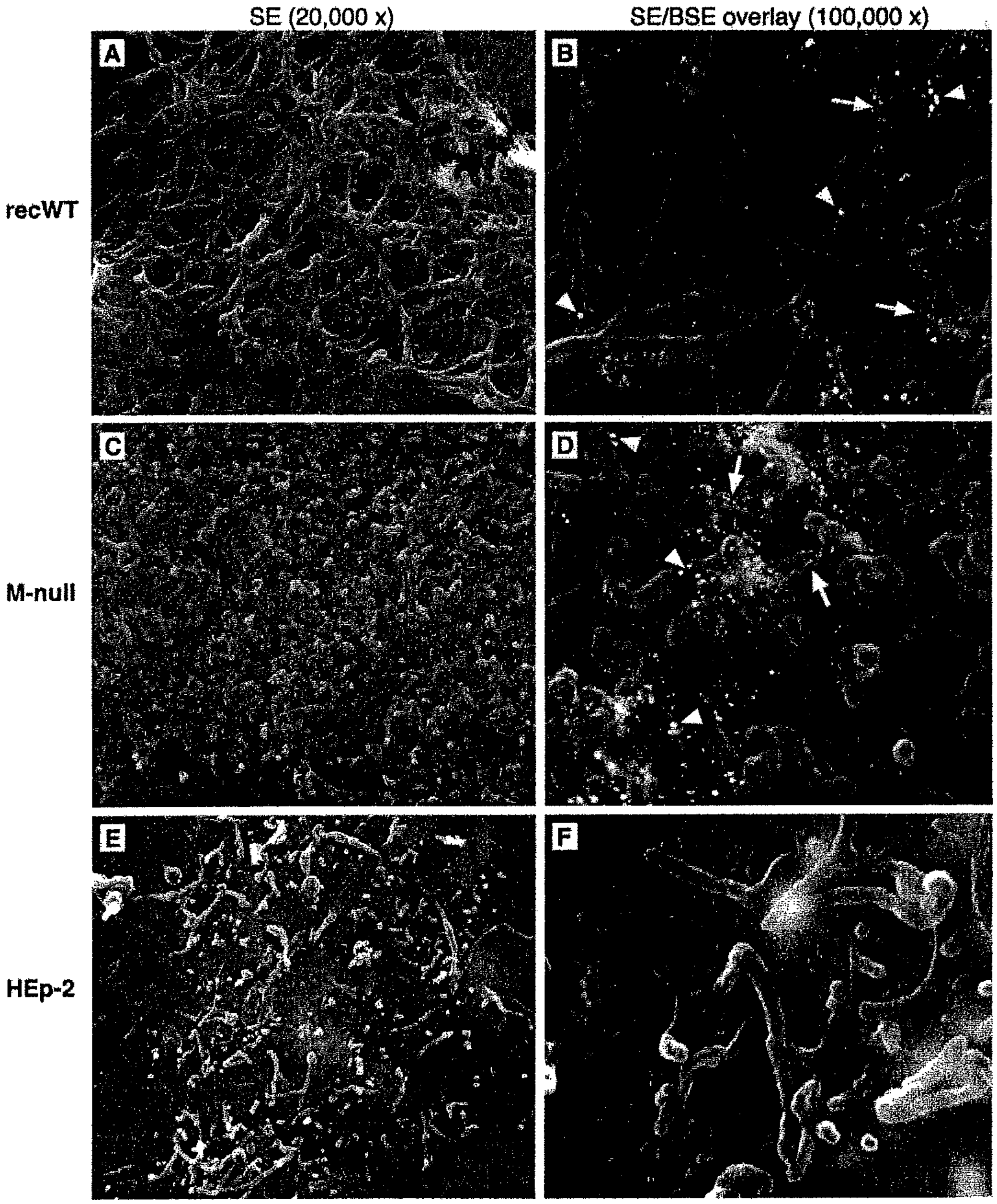
FIG. 5. High resolution analysis of the surface of M-null virus infected cells. HEp-2 cells were infected as described in FIG. 3A with viruses recWT (panels A, B) or M-null (panels C, D), or left uninfected (panels E, F). At 26 hpi, cells were incubated stepwise with anti-G (L9) and anti-F (Synagis) antibodies and goat-anti-mouse or goat-anti-human antibodies conjugated to 15 nm and 25 nm colloidal gold respectively, and processed for Field emission SEM analysis as described in Materials and Methods. Samples (approximately 25 fields containing infected cells) were examined with SEM, and scanned at 20,000× magnification using secondary electron detection mode (SE)(panels A, C, E) and at 100,000× using both SE and backscattered electron (BSE) detection modes to also visualize gold particles. Photographs of SE and BSE scans were overlaid (panels B, D, F). White arrowheads indicate 25 nm gold particles (F protein), white arrows indicate 15 nm gold particles (G protein).

To ask whether the inability to detect viral filaments in M-null virus infected cells by IF microscopy (FIG. 4) represented a failure of filament formation or of viral protein targeting to existing filaments, the surface of M-null and recWT infected cells was examined at higher resolution. A procedure described by Jeffree et al (31) was applied in which field emission SEM was combined with immunogold labeling (FIG. 5). Infected cells were fixed at 26 hpi, labeled with anti-G and F antibodies and secondary antibodies conjugated to 15 or 25 nm gold respectively, and processed for SEM as described in Materials and Methods. Fields in the samples were analyzed at various magnifications and photographed at 20,000× using secondary electron (SE) detection mode to visualize surface filaments (panels A, C, E) and 100,000× using both SE and backscattered electron (BSE) detection modes to also identify gold particles bound to the G and F proteins (panels B, D, F). At 20,000× magnification, the cell surface of recWT virus infected cells displayed an abundance of filaments (FIG. 5, panel A). Such filaments have been reported previously and were not detected at the surface of uninfected cells (FIG. 5, panel E). Immunogold labeling and overlay of SE and BSE images provided further evidence that the identified cells were indeed infected (FIG. 5, panel B). Fewer 25 nm particles (F protein) than 15 nm particles (G protein) were observed, which may be a consequence of variation in antibody binding kinetics and size of gold particles, or reflect a high G:F protein ratio in viral filaments. Despite the failure to detect filament structures by IF microscopy in FIG. 4, SEM analysis of M-null virus infected cells revealed an abundance of densely packed short filaments, often covering the majority of the available cell surface (FIG. 5, panels C and D). Both the diameter of the short filaments and the extent of G and F labeling by gold particles, were similar to those of filaments induced by the recWT virus. The uniformity of length and appearance of the short filaments on M-null virus infected cells (FIG. 5, panel C), suggest that these filaments did not develop normally after initiation. The data thus indicate that while the M protein is not required for the initial stage of virus-induced surface filament formation, in its absence filaments fail to elongate or mature properly.

Discussion

A better understanding of HRSV assembly will help overcome challenges in the current vaccine strategies and may lead to new opportunities for HRSV therapeutics. This study addresses the role of the viral M protein, and shows that M is a critical factor in the organization of infectious progeny production. Filamentous virions have been described as the predominant infectious HRSV virion phenotype in cell culture, even after extensive passage, and do not appear to be a tissue culture adaptation. However, their relative abundance in vivo, or the role that the cell surface-attached filaments might play in virus dissemination within an infected host, is not understood. Irrespective of the in vivo significance, detailed knowledge of the assembly process of viral filaments in cell culture is important, as vaccine manufacture, be it live-attenuated, killed, or in the form of virus-like-particles, will most likely depend on a cell culture platform. In addition, the M protein of HRSV has unique characteristics within the paramyxoviruses, among which the absence of a known viral Late domain and structural similarity with the VP40 matrix protein of Ebola virus (33, 38). Hence, characterizing the role of the M protein in viral assembly may also provide novel insights in viral replication mechanisms.

This study describes the generation and characterization of an M-null virus, and its use in dissecting the role of the M protein in late-stage viral assembly. A null virus approach was used because of potential downstream advantages such as the generation of viruses with debilitating M mutations for in vivo studies. Through complementation of M protein by an M-expressing cell line, it was possible able to generate infectious virus stocks lacking an intact M protein gene. The resulting infectious M-null virus allowed for the first time investigation of the HRSV infection cycle in the complete absence of M. It is important to keep in mind that this study was done in the absence of the viral SH protein. Prior studies do not suggest a major role for the SH protein in viral assembly or filament formation, and the instant inventor's results are in agreement with these previous findings. However, a minor direct or indirect impact of SH on filament production in vitro, or a possible significant impact in vivo, cannot be excluded by the presented data.

Characterization of the M-Null Virus.

Titers of M-null virus stocks were generally low (approximately $10^5$ PFU/ml), which may reflect cytotoxic effects by M during amplification in H2-M cells or suboptimal processing or spatio-temporal regulation of M when expressed from the host cell nucleus. Analysis of protein expression by ELISA showed that expression of other viral proteins was moderately higher in the absence of M. The previously reported inhibition of host and viral transcription by M (18, 21) may explain the overall increase in HRSV protein expression levels in the absence of M.

The M Protein is Critical for Infectious Virus Production.

An important role for M in virion production was anticipated based on a previously reported HRSV minireplicon system (58) and analogy to the roles of M proteins from other paramyxoviruses (12, 29, 40, 46). The growth analysis shown in FIG. 3 directly demonstrates that HRSV M is critical for production of both released and cell-associated infectious progeny. In the absence of M, infectious virus production was reduced by ~1,000 to 10,000 fold. Whether the remaining infectivity represents true infectious progeny production in the absence of M, or is a result of experimental conditions of the sensitive flow cytometry based assay, is not known. Syncytium formation was observed in both recWT and M-null virus infected cell cultures. This was not surprising since expression of the F protein alone is capable of inducing extensive cell-cell membrane fusion (5, 26). In the absence of M however syncytia were limited in size, and healthy uninfected cells in the culture kept dividing throughout the analysis. In contrast, an M-lacking measles virus, which also showed strongly reduced titers, was reported to propagate through a Vero cell culture as efficiently as wt measles virus due to enhanced cell-cell fusion (12). These differences may be the result of the unique properties of closely related viruses. In case of Sendai virus, another paramyxovirus, it was shown that VLPs were not or poorly generated when M expression was suppressed (40). While these data show that HRSV infectious progeny production was nearly abrogated in the absence of M, the possibility that non-infectious VLPs were released cannot be excluded.

The Role of the M Protein in Viral Filament Formation.

HRSV-induced surface filaments have been suggested to be the equivalent of virions (27, 49, 53, 60), and loss of viral filaments typically results in loss of the majority of viral infectivity (7, 42, 49, 53). An exception to the above was a study in which wt HRSV-infected HEp-2 cells were treated with RhoA inhibitors (22). In those instances, the amount of surface filaments was strongly reduced but the yield of infectious virus was unchanged relative to untreated cells. Moreover, gradient fractionation and EM analysis showed that upon treatment with RhoA inhibitors, virion morphology shifted from predominantly filamentous to predominantly spherical. Whether more than one infectious HRSV morphology exists in vivo, and whether distinct morphologies might have distinct roles is not known. Similarly, the machinery and mechanisms that underlie the abundant filament formation observed in cell culture are not understood. Studies conducted by the instant inventor provide new insights into the process of viral filament formation. By IF microscopy (FIG. 4) the typical N, G, and F containing filaments were notably absent in M-null virus infected cells. Instead the N protein accumulated in IBs while G and to a lesser degree F. were present at the plasma membrane in an evenly distributed but punctate manner. High resolution analysis of the surface of M-null virus infected cells (FIG. 5) revealed the presence of abundant, uniformly short, G and F-containing filaments, with a diameter similar to those seen in wt virus infected cells. Though both IF and SEM analyses thus demonstrate clear differences in filament formation in the absence versus the presence of M, the contrast in G and F targeting appeared greater when analyzed by IF microscopy. This may be related to the ease with which G and F proteins on the cell surface are labeled during the IF procedure, and the significantly more challenging and non-quantitative labeling of G and F proteins associated with the SEM protocol.

The uniformity of the short filaments on M-null virus infected cells is highly suggestive of an assembly process that was initiated but arrested. It thus appears that M is not required for the initiation of virus-induced surface filaments, but the filaments are unable to elongate in M's absence. These observations appear to be in agreement with the recent findings that M has an intrinsic property to self-assemble into helical arrays, when incubated in the presence of select lipid mixtures (37). While the latter finding points to a capacity for M to drive both filament initiation and elongation, the abundance of stunted filaments on M-null virus infected cells suggests that other viral factors, or processes induced after viral infection, are capable of initiating filament formation in M's absence. A role for the F protein in driving filament formation was suggested by another study in which IBs and growing filaments were occasionally found in close proximity, with F and P proteins co-localizing in projections originating from the IBs (30, 49). In addition, in the absence of the F protein cytoplasmic tail (CT), infectious virus production was nearly abrogated and viral filaments could not be detected by anti-F and G antibodies (42). The presence of G and F proteins in stunted filaments (FIG. 5) may support an M-independent role for F, or F and G proteins combined, in filament initiation. However, the non-quantitative labeling in the presented SEM data do not exclude the possibility that G and F proteins are associated with stunted filaments by their mere presence at the plasma membrane, especially in the case of the surface-abundant G protein. Furthermore, VLPs were found to be released from polarized cells with high efficiency in the absence of the glycoproteins (2, 3). Although the morphology of the released VLPs was not examined, it indicates that the remaining viral proteins (which include M) can efficiently drive budding of particles in the complete absence of the glycoproteins. In short, further studies are needed to establish the relative contribution of the M, G and F proteins in initiation of viral filament formation.

RNP Transport: IBs, M, and the Cytoskeleton.

Cytoplasmic IBs are believed to be sites of RNP production. M was previously shown both to target to cytoplasmic IBs at a stage of the infection cycle prior to virion release, and to associate with RNPs via interaction with the M2-1 protein (21, 35), presumably to shut down RNA synthesis and initiate the assembly process. The M2-1 dependent association of M with viral RNPs differs from the reported findings of other paramyxovirus M proteins, in which biochemical and IF microscopy-based evidence suggests a direct interaction between M and N proteins (25). The above reports, as well as the observed presence of growth-arrested viral filaments in the absence of M (FIG. 5) and simultaneous increase of N presence in IBs (FIG. 4), support a model in which the M proteins are involved in targeting RNPs to budding sites. How HRSV M-RNP complexes would be transported from IBs to sites of budding is not known but likely involves the cytoskeleton. Several cytoskeletal proteins, among which actin isoforms, cofilin, and filamin-1, were detected by mass spectrometry analysis of purified viral filaments (though purity was hard to assess due to the cell-associated nature of filaments). There is ample evidence of a role for polymerized actin and actin-regulatory proteins in assembly (4, 6, 11, 22, 30, 32, 49, 53, 59). However the role of polymerized actin seems to be limited to the actual budding/release event (11, 30, 32), which was shown to occur at sites of lipid rafts (8, 9, 22, 27, 31, 36, 42, 49, 50). In contrast to oftlinepolymerized actin, microtubules were reported to be involved in virus production at a step prior to budding (32). Though the role of cytoskeletal components in RNP transport are thus far from understood, the instant inventor's data implicates the M protein in this process. Alternatively, RNP transport to sites of budding continues in the absence of M but M-lacking RNPs fail to reach destination or to support filament elongation once arrived. The latter would seem inconsistent with the observed accumulation of N in IBs of M-null virus infected cells.

In Conclusion.

An improved understanding of the origin and formation of viral filaments in cell culture is important, because these filaments represent the majority of HRSV infectivity and cell culture is the manufacturing platform for current candidate vaccine stocks. The presented work for the first time allowed examination of infected cells in the complete absence of M protein, and showed that M plays a role in maturation and/or maintenance of viral filaments. The increased presence of the N protein in IBs in the absence of M suggests this role may be played through interaction of M with RNPs, and subsequent transport of the resulting complexes to sites of filament production. Currently, the M-null system is being developed to serve as a platform to further probe the mechanisms underlying assembly, and the role of the M protein therein.

The above results demonstrate the principle of controlling RSV infectivity by manipulating the essential M protein. Importantly, the successful generation of a virus lacking M for the first time, now allows generation of engineered viruses with any desired, deleterious M content. This in turn enables production of RSV viruses with controlled cell-to-cell transmission, providing novel options for vaccine safety.

All references cited herein are hereby incorporated by reference in entirety.

References for Example 1

1. Bachi, T., and C. Howe. 1973. Morphogenesis and ultrastructure of respiratory syncytial virus. J Virol 12:1173-80.
2. Batonick, M., A. G. Oomens, and G. W. Wertz. 2008. Human respiratory syncytial virus glycoproteins are not required for apical targeting and release from polarized epithelial cells. J Virol 82:8664-72.
3. Batonick, M., and G. W. Wertz. 2011. Requirements for Human Respiratory Syncytial Virus Glycoproteins in Assembly and Egress from Infected Cells. Adv Virol 2011.
4. Bitko, V., A. Oldenburg, N. E. Garmon, and S. Barik. 2003. Profilin is required for viral morphogenesis, syncytium formation, and cell-specific stress fiber induction by respiratory syncytial virus. BMC Microbiol 3:9.
5. Branigan, P. J., C. Liu, N. D. Day, L. L. Gutshall, R. T. Sarisky, and A. M. Del Vecchio. 2005. Use of a novel cell-based fusion reporter assay to explore the host range of human respiratory syncytial virus F protein. Virol J 2:54.
6. Brock, S. C., J. R. Goldenring, and J. E. Crowe, Jr. 2003. Apical recycling systems regulate directional budding of respiratory syncytial virus from polarized epithelial cells. Proceedings of the National Academy of Sciences of the United States of America 100:15143-8.
7. Brock, S. C., J. M. Heck, P. A. McGraw, and J. E. Crowe, Jr. 2005. The transmembrane domain of the respiratory syncytial virus F protein is an orientation-independent apical plasma membrane sorting sequence. J Virol 79:12528-35.
8. Brown, G., J. Aitken, H. W. Rixon, and R. J. Sugrue. 2002. Caveolin-1 is incorporated into mature respiratory syncytial virus particles during virus assembly on the surface of virus-infected cells. J Gen Virol 83:611-21.

9. Brown, G., C. E. Jeffree, T. McDonald, L. R. H. W. Mc, J. D. Aitken, and R. J. Sugrue. 2004. Analysis of the interaction between respiratory syncytial virus and lipid-rafts in Hep2 cells during infection. Virology 327:175-85.
10. Bukreyev, A., S. S. Whitehead, B. R. Murphy, and P. L. Collins. 1997. Recombinant respiratory syncytial virus from which the entire SH gene has been deleted grows efficiently in cell culture and exhibits site-specific attenuation in the respiratory tract of the mouse. J Virol 71:8973-82.
11. Burke, E., L. Dupuy, C. Wall, and S. Barik. 1998. Role of cellular actin in the gene expression and morphogenesis of human respiratory syncytial virus. Virology 252: 137-48.
12. Cathomen, T., H. Y. Naim, and R. Cattaneo. 1998. Measles viruses with altered envelope protein cytoplasmic tails gain cell fusion competence. J Virol 72:1224-34.
13. Chen, B. J., and R. A. Lamb. 2008. Mechanisms for enveloped virus budding: can some viruses do without an ESCRT? Virology 372:221-32.
14. Collins, P. L., Y. T. Huang, and G. W. Wertz. 1984. Nucleotide sequence of the gene encoding the fusion (F) glycoprotein of human respiratory syncytial virus. Proc Natl Acad Sci USA 81:7683-7.
15. Couch, R. B., J. A. Englund, and E. Whimbey. 1997. Respiratory viral infections in immunocompetent and immunocompromised persons. The American journal of medicine 102:2-9; discussion 25-6.
16. Fuchs, H., and T. Bachi. 1975. Scanning electron microscopical demonstration of respiratory syncytial virus antigens by immunological markers. Journal of ultrastructure research 52:114-9.
17. Garcia, J., B. Garcia-Barreno, A. Vivo, and J. A. Melero. 1993. Cytoplasmic inclusions of respiratory syncytial virus-infected cells: formation of inclusion bodies in transfected cells that coexpress the nucleoprotein, the phosphoprotein, and the 22K protein. Virology 195:243-7.
18. Ghildyal, R., C. Baulch-Brown, J. Mills, and J. Meanger. 2003. The matrix protein of Human respiratory syncytial virus localises to the nucleus of infected cells and inhibits transcription. Arch Virol 148:1419-29.
19. Ghildyal, R., A. Ho, and D. A. Jails. 2006. Central role of the respiratory syncytial virus matrix protein in infection. FEMS Microbiol Rev 30:692-705.
20. Ghildyal, R., D. Li, I. Peroulis, B. Shields, P. G. Bardin, M. N. Teng, P. L. Collins, J. Meanger, and J. Mills. 2005. Interaction between the respiratory syncytial virus G glycoprotein cytoplasmic domain and the matrix protein. J Gen Virol 86:1879-84.
21. Ghildyal, R., J. Mills, M. Murray, N. Vardaxis, and J. Meanger. 2002. Respiratory syncytial virus matrix protein associates with nucleocapsids in infected cells. J Gen Virol 83:753-7.
22. Gower, T. L., M. K. Pastey, M. E. Peeples, P. L. Collins, L. H. McCurdy, T. K. Hart, A. Guth, T. R. Johnson, and B. S. Graham. 2005. RhoA signaling is required for respiratory syncytial virus-induced syncytium formation and filamentous virion morphology. J Virol 79:5326-36.
23. Haas, J., E. C. Park, and B. Seed. 1996. Codon usage limitation in the expression of HIV-1 envelope glycoprotein. Curr Biol 6:315-24.
24. Han, L. L., J. P. Alexander, and L. J. Anderson. 1999. Respiratory syncytial virus pneumonia among the elderly: an assessment of disease burden. The Journal of infectious diseases 179:25-30.
25. Harrison, M. S., T. Sakaguchi, and A. P. Schmitt. 2010. Paramyxovirus assembly and budding: building particles that transmit infections. Int J Biochem Cell Biol 42:1416-29.
26. Heminway, B. R., Y. Yu, Y. Tanaka, K. G. Perrine, E. Gustafson, J. M. Bernstein, and M. S. Galinski. 1994. Analysis of respiratory syncytial virus F, G, and SH proteins in cell fusion. Virology 200:801-5.
27. Henderson, G., J. Murray, and R. Yeo. 2002. Sorting of the respiratory syncytial virus matrix protein into detergent-resistant structures is dependent on cell-surface expression of the glycoproteins. Virology 300:244.
28. Huang, Y. T., P. L. Collins, and G. W. Wertz. 1985. Characterization of the 10 proteins of human respiratory syncytial virus: identification of a fourth envelope-associated protein. Virus research 2:157-73.
29. Inoue, M., Y. Tokusumi, H. Ban, T. Kanaya, M. Shirakura, T. Tokusumi, T. Hirata, Y. Nagai, A. Iida, and M. Hasegawa. 2003. A new Sendai virus vector deficient in the matrix gene does not form virus particles and shows extensive cell-to-cell spreading. J Virol 77:6419-29.
30. Jeffree, C. E., G. Brown, J. Aitken, D. Y. Su-Yin, B. H. Tan, and R. J. Sugrue, 2007. Ultrastructural analysis of the interaction between F-actin and respiratory syncytial virus during virus assembly. Virology 369:309-23.
31. Jeffree, C. E., H. W. Rixon, G. Brown, J. Aitken, and R. J. Sugrue. 2003. Distribution of the attachment (G) glycoprotein and GM1 within the envelope of mature respiratory syncytial virus filaments revealed using field emission scanning electron microscopy. Virology 306:254-67.
32. Kallewaard, N, L., A. L. Bowen, and J. E. Crowe, Jr. 2005. Cooperativity of actin and microtubule elements during replication of respiratory syncytial virus. Virology 331:73-81.
33. Latiff, K., J. Meanger, J. Mills, and R. Ghildyal. 2004. Sequence and structure relatedness of matrix protein of human respiratory syncytial virus with matrix proteins of other negative-sense RNA viruses. Clin Microbiol Infect 10:945-8.
34. Levine, S., R. Klaiber-Franco, and P. R. Paradiso. 1987. Demonstration that glycoprotein G is the attachment protein of respiratory syncytial virus. J Gen Virol 68:2521-4.
35. Li, D., D. A. Jans, P. G. Bardin, J. Meanger, J. Mills, and R. Ghildyal. 2008.
Association of respiratory syncytial virus M protein with viral nucleocapsids is mediated by the M2-1 protein. J Virol 82:8863-70.
36. McCurdy, L. H., and B. S. Graham. 2003. Role of plasma membrane lipid microdomains in respiratory syncytial virus filament formation. J Virol 77:1747-56.
37. McPhee, H. K., J. L. Carlisle, A. Beeby, V. A. Money, S. M. Watson, R. P. Yeo, and J, M. Sanderson. 2011. Influence of lipids on the interfacial disposition of respiratory syncytical virus matrix protein. Langmuir 27:304-11.
38. Money, V. A., H. K. McPhee, J. A. Mosely, J. M. Sanderson, and R. P. Yeo. 2009. Surface features of a Mononegavirales matrix protein indicate sites of membrane interaction. Proc Natl Acad Sci USA 106:4441-6.
39. Morton, C. J., R. Cameron, L. J. Lawrence, B. Lin, M. Lowe, A. Luttick, A. Mason, J. McKimm-Breschkin, M. W. Parker, J. Ryan, M. Smout, J. Sullivan, S. P. Tucker, and P. R. Young. 2003. Structural characterization of respiratory syncytial virus fusion inhibitor escape mutants: homology model of the F protein and a syncytium formation assay. Virology 311:275-88.

40. Mottet-Osman, G., F. Iseni, T. Pelet, M. Wiznerowicz, D. Garcin, and L. Roux. 2007. Suppression of the Sendai virus M protein through a novel short interfering RNA approach inhibits viral particle production but does not affect viral RNA synthesis. J Virol 81:2861-8.
41. Norrby, E., H. Marusyk, and C. Orvell. 1970. Morphogenesis of respiratory syncytial virus in a green monkey kidney cell line (Vero). Journal of virology 6:237-42.
42. Oomens, A. G., K. P. Bevis, and G. W. Wertz. 2006. The cytoplasmic tail of the human respiratory syncytial virus F protein plays critical roles in cellular localization of the F protein and infectious progeny production. J Virol 80:10465-77.
43. Oomens, A. G., A. G. Megaw, and G. W. Wertz. 2003. Infectivity of a human respiratory syncytial virus lacking the SH, G, and F proteins is efficiently mediated by the vesicular stomatitis virus G protein. J Virol 77:3785-98.
44. Oomens, A. G., and G. W. Wertz. 2004. The baculovirus GP64 protein mediates highly stable infectivity of a human respiratory syncytial virus lacking its homologous transmembrane glycoproteins. J Virol 78:124-35.
45. Oomens, A. G., and G. W. Wertz. 2004. trans-Complementation allows recovery of human respiratory syncytial viruses that are infectious but deficient in cell-to-cell transmission. J Virol 78:9064-72.
46. Peeples, M. E. 1991. Paramyxovirus M proteins: Pulling it all together and taking it on the road. Plenum Press, New York.
47. Petrakova, O., E. Volkova, R. Gorchakov, S. Paessler, R. M. Kinney, and I. Frolov. 2005. Noncytopathic replication of Venezuelan equine encephalitis virus and eastern equine encephalitis virus replicons in Mammalian cells. J Virol 79:7597-608.
48. Pringle, C. R. 1987. Progress towards control of the acute respiratory viral diseases of childhood. Bulletin of the World Health Organization 65:133-7.
49. Radhakrishnan, A., D. Yeo, G. Brown, M. Z. Myaing, L. R. Iyer, R. Fleck, B. H. Tan, J. Aitken, D. Sanmun, K. Tang, A. Yarwood, J. Brink, and R. J. Sugrue. 2010. Protein analysis of purified respiratory syncytial virus particles reveals an important role for heat shock protein 90 in virus particle assembly. Mol Cell Proteomics 9:1829-48.
50. Rixon, H. W., G. Brown, J. Aitken, T. McDonald, S. Graham, and R. J. Sugrue. 2004. The small hydrophobic (SH) protein accumulates within lipid-raft structures of the Golgi complex during respiratory syncytial virus infection. J Gen Virol 85:1153-65.
51. Roberts, S. R., R. W. Compans, and G. W. Wertz. 1995. Respiratory syncytial virus matures at the apical surfaces of polarized epithelial cells. J Virol 69:2667-73.
52. Rodriguez, L., I. Cuesta, A. Asenjo, and N. Villanueva. 2004. Human respiratory syncytial virus matrix protein is an RNA-binding protein: binding properties, location and identity of the RNA contact residues. J Gen Virol 85:709-19.
53. Santangelo, P. J., and G. Bao. 2007. Dynamics of filamentous viral RNPs prior to egress. Nucleic acids research 35:3602-11,
54. Schmitt, A. P., and R. A. Lamb. 2004. Escaping from the cell: assembly and budding of negative-strand RNA viruses. Curr Top Microbiol Immunol 283:145-96.
55. Stope, M. B., A. Karger, U. Schmidt, and U. J. Buchholz. 2001. Chimeric bovine respiratory syncytial virus with attachment and fusion glycoproteins replaced by bovine parainfluenza virus type 3 hemagglutinin-neuraminidase and fusion proteins. J Virol 75:9367-77.
56. Takimoto, T., and A. Portner. 2004. Molecular mechanism of paramyxovirus budding. Virus Res 106:133-45.
57. Tayyari, F., D. Marchant, T. J. Moraes, W. Duan, P. Mastrangelo, and R. G. Hegele. 2011. Identification of nucleolin as a cellular receptor for human respiratory syncytial virus. Nature medicine.
58. Teng, M. N., and P. L. Collins. 1998. Identification of the respiratory syncytial virus proteins required for formation and passage of helper-dependent infectious particles. J Virol 72:5707-16.
59. Ulloa, L., R. Serra, A. Asenjo, and N. Villanueva. 1998. Interactions between cellular actin and human respiratory syncytial virus (HRSV). Virus research 53:13-25.
60. Utley, T. J., N. A. Ducharme, V. Varthakavi, B. E. Shepherd, P. J. Santangelo, M. E. Lindquist, J. R. Goldenring, and J. E. Crowe, Jr. 2008. Respiratory syncytial virus uses a Vps4-independent budding mechanism controlled by Rab11-FIP2. Proc Natl Mad Sci USA 105: 10209-14.

Example 2. Scan Mutations of M Protein

FIG. 6 shows the nucleotide sequence encoding the unmodified M gene from RSV A2 strain (FIG. 6A) and the sequence of the codon-optimized M gene used to generate M-expressing cells (FIG. 6B). FIG. 7 shows the amino acid sequence of unmodified M protein from the RSV A2 strain.

Scan mutation assays, which replace selected amino acids in the primary sequence of a protein with different amino acids, usually sequentially along the length of the protein sequence, are known in the art and are used to identify sections of the protein that are required or important for activity. FIGS. 8A and B show exemplary mutants of M protein derived by inserting an epitope of 9 amino acids in a scanning fashion at various positions along the length of the M protein.

As recognized in the art, alanine scanning mutations are a more specific type of scanning assay. In this method, each (or selected) amino acid residues of a protein sequence of interest are replaced with alanine. Consecutive adjacent single residues may be replaced one at a time by Ala, or selected single residues may be replaced, or, in double Ala scanning, one or more groups of two adjacent residues are both replaced by Ala. This procedure can be used to create a family of mutant proteins, each member of the family having a plurality of selected residues replaced by Ala. This technique permits investigation of the impact of each of these point or substitution mutations on activity, function, structure, etc. of the sequence that is mutated. Examples of mutant M proteins with double alanine mutations are shown in FIGS. 8C-F.

Double alanine scanning was used to mutate the M gene in this manner. Twenty double alanine substitution mutants in amino acid region 116-155 of the M protein were constructed and the sequences of these 20 mutant proteins are shown in FIGS. 9A-T. Plasmids comprising nucleotide sequences encoding each of the mutants were transfected into cells infected with the M-null virus making it possible to determine in a simple assay the level at which each of the M mutants complemented the M-null virus, and thus to observe the impact of the mutations on virus infectivity. The amount of infectious virus produced in cells harboring the mutant viruses was measured using flow cytometry. FIG. 10 depicts the results that were obtained. As can be seen, the results show that even within small regions of the M protein (e.g., as few a 2 adjacent amino acids), mutations can be identified that increase, abolish, or diminish virus infectivity.

For example, replacement of residues 122/123, 132/133, and 154/155 with Ala increases viral production almost 2-fold above that of wild type. Without being bound by theory, it is believed that these mutations improve the level of infectivity because the mutant M protein is better tolerated than wt M, or expressed at a higher level than wt M, or both, when expressed in cells. In contrast, replacement at residues 116/117, 126/127, and 150/151 (and others) essentially abolish viral reproduction. Replacement of some residues have an intermediate effect (e.g., mutant 130/131, which has approximately 40% of the activity of wt M. Those of skill in the art will recognize that further studies of this type can be carried out for the entire length of the M protein, i.e., any two adjacent residues can be mutated in this manner, or, alternatively, any single residue can be mutated by replacement with alanine (or another residue such as glycine if the residue is alanine), and the results can be analyzed and mutants of interest selected in a similar fashion.

The amino acids residues that have been identified are significant with respect to modifying M protein activity provide information regarding the underlying mechanisms of action of the M protein, and are candidates for re-engineering back into the viral genome to make attenuated viruses suitable for use in vaccines. In particular, based on information from such scans, amino acid residues of M protein have been and are identified which impact the activity of M in different ways, permitting the tailoring or purposeful design (tuning, fine tuning) of attenuated viruses with desired properties, e.g., with various levels of infectivity, with various levels of ability to spread from cell-to-cell, with various levels of impact on virion stability, with varying virion morphology, with various levels of virus entry, with various levels of host immune dysregulation or host cell cycle dysregulation, etc. Viruses so-constructed have varying abilities to elicit an immune response in a host in an efficacious and yet safe manner, and permit the purposeful design of vaccines with varying levels of antigenicity. For example, for vaccinating individuals with immature or compromised immune systems (e.g., infants, HIV patients, the elderly, etc.), a less robust (e.g., less antigenic) vaccine may be required whereas for a healthy adult with a normal immune response, a more robust vaccine may be necessary.

Such mutants can also be used, for example, in the production and manufacture of virus-like particles (VLP). The construction of VLPs for use in vaccines is currently of great interest because VLPs lack the viral genome and so are perceived safe for use. VLPs are typically made in cell culture by introducing several structural viral proteins, the base ingredient of which is always M. However, there are reports of very low virus yields from such systems, yields which are not even sufficient to allow testing in animals. The present finding that some M mutants (mutants 122/123, 132/133, 152/153, and 154/155) are expressed more highly than wt M and yield higher amounts of infectious virus when complementing the M-null virus, indicates these mutants would be likely to improve VLP production yields. Moreover, the screening system described above allows screening for additional M variants that may further benefit VLP production. Thus, the screening system represents a novel method to discover M variants that will help overcome difficulties in VLP production. It should be understood that the above-described embodiments and the following examples are given by way of illustration, not limitation. Various changes and modifications within the scope of the invention will become apparent to those skilled in the art from the present description.

Example 3

In Examples 1 and 2, a system was used to test mutant M protein in which a recombinant attenuated virus with a “first generation” mutant M-null protein also expressed a tet transactivating protein, and induction of expression of M was carried out in a cell line carrying the M gene under control of tet-responsive elements (TRE). The first generation M-null construct is depicted schematically in FIG. 11 (see middle section of figure). In this system, the M protein is expressed from the plasmids in all cells after induction with doxycyclin, whether or not virus from a mutant M sequence is replicating in the cells, resulting in cytotoxic effects to the cell culture prior to the viral exploitation of the cell for amplification of the mutant M protein. The titers obtained in such systems are generally low (~$10^5$ PFU/ml) and the cytotoxic effect on H2-M cells is most likely the reason, or one of the reasons, underlying the low titers. The problems/challenges of the first generation M-null construct are described in detail in FIG. 12A.

In order to demonstrate that the system is amenable to modification for higher virus titers, a new second generation M-null system was designed in which the cell line in which the virus propagates contains a plasmid encoding the tetracycline response elements (encoded by the TRE-M gene), but in which other elements necessary for activation of TRE-M (i.e., the Tet transactivating protein) are present on the viral genome of a second generation virus that is used to infect the host cell (see bottom of FIG. 11). The second generation M-null virus contains EGFP ORF in place of the SH ORF, but contains the tet-off transactivator gene (ORF) in place of M. The second generation M-null virus was recovered from cDNA, and was successfully used to infect host cells. The results showed that uninfected cells do not express the M protein and remain viable and available for amplification and for infection. This second generation M-null system is described in detail in FIG. 12B.

Further, instead of wt M, the particular M mutants used to create the second generation M-null virus were double alanine mutants M122/123 and 132/133. These mutants were chosen because they had been shown to increase infectious virus production (see FIG. 10). Two new cell lines (HTM-34 and HTM-51) were generated, each of which expresses an M mutant under control of the TRE. Titration of M-null second generation stocks, produced in HTM-34 cells, indicated that the titer of this second generation M-null virus was $10^6$ PFU/ml (without freeze/thaw step), 1 log (10-fold) higher than the first generation M-null virus described above. This experiment thus demonstrates that the use of inducible promoters (not limited to the tet system here demonstrated) can be used to generate M-recombinant viruses to titers approaching wt level titers. This increase in viral titer has applications, for example, in the production of viruses for use in vaccines.

Example 4. Inducible Host Cell/Mini-Replicon System

As another example of transactivation by the virus of an inducible element in the host cell line, a cell line is constructed expressing an RSV ‘mini-replicon’ encoding the M protein. A mini-replicon is a shortened version of the viral genome from which all or part of the coding regions have been removed, but which retains the 5' and 3' ends of the viral genome. Mini-replicons are well characterized and understood by those skilled in the art but have not been utilized for the purposes proposed here. According to the present invention, the M gene only would be re-inserted into the mini-replicon. The mini-replicon would be inserted into a plasmid preceded by any promoter recognized by the host cell machinery and followed by a ribozyme sequence or another termination sequence. A cell line is constructed which constitutively expresses the mini-replicon. However, the mini-replicon requires the viral polymerase to amplify and express the M protein. Therefore, the replicon will be amplified only in the presence of M-null virus, after which high levels of M protein will be produced. The 3' and 5' ends of the mini-replicon will be mutated to generate a variant that cannot be packaged into virions, so as to serve only the purpose of amplification of M protein for production of M-variant viruses. In case of M expression by a mini-replicon, the M-null virus does not need to contain a non-viral inducible element because the viral polymerase produced by the M-null virus would be sufficient to start replicon amplification. However, it could be engineered to be dependent on an inducible element, if needed.

This system may also be used to evaluate the activity/infectivity of mutant M proteins.

Example 5. Use of a Vaccine Preparation Comprising the Viruses of the Invention

An RSV vaccine preparation of the invention is administered to a subject in need thereof. As a result of administration, the subject is resistant to further infection by RSV, or symptoms of infection by RSV are much less severe than if the vaccine had not been administered.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A recombinant, live, non-disseminating respiratory syncytial virus (RSV) in which a gene or open reading frame (ORF) encoding a matrix (M) protein is deleted from the viral genome, wherein said recombinant, live, non-disseminating RSV comprises an M protein produced by a host cell that is genetically engineered to encode and express the M protein, and wherein said recombinant, live, non-disseminating RSV is capable of infecting one or more host cells when initially administered to a subject, but, once administered, generates no progeny, or progeny that are unable to disseminate.

2. The recombinant, live, non-disseminating RSV of claim 1, wherein viral RNA replication and transcription are not attenuated.

3. The recombinant, live, non-disseminating RSV of claim 1, wherein the host cell is genetically engineered to encode and express the M protein from the host cell genome or from a plasmid.

4. The recombinant, live, non-disseminating RSV of claim 1, wherein the recombinant, live non-disseminating RSV encodes at least one transactivation element that induces production of the M protein by the host cell.

5. The recombinant, live, non-disseminating virus of claim 1, wherein the RSV is human RSV.

6. A pharmaceutical composition comprising a recombinant, live, non-disseminating, respiratory syncytial virus (RSV) in which a gene or open reading frame (ORF) encoding a matrix (M) protein is deleted from the viral genome, wherein said recombinant, live, non-disseminating, RSV comprises a M protein produced by a host cell that is genetically engineered to encode and express the M protein, and wherein said recombinant, live, non-disseminating, RSV is capable of infecting one or more host cells when initially administered to a subject, but, once administered, generates no progeny, or progeny that are unable to disseminate, and wherein said recombinant, live, non-disseminating, virus is present in said pharmaceutical composition in an amount sufficient to elicit an immune response in a host.

7. The pharmaceutical composition of claim 6 wherein the recombinant, live, non-disseminating, RSV encodes at least one transactivation element that induces production of the M protein by the host cell.

8. A method of immunizing a subject against symptoms of disease caused by RSV, comprising the step of administering to said subject at least one dose of the pharmaceutical composition of claim 6.

9. The method of claim 8, wherein said subject is selected from the group consisting of an adult, a child, an immunocompromised individual, and an elderly individual.

10. A non-disseminating, recombinant, live respiratory syncytial virus (RSV), wherein said non-replicating recombinant, live RSV comprises an RSV genome which lacks a gene encoding an M protein, and comprises an M protein produced by a host cell.

11. The non-disseminating, recombinant, live RSV of claim 10, wherein the M protein is produced by a transfected cell from a trans-complementing cell line.

12. The non-disseminating, recombinant, live RSV of claim 10, wherein said non-disseminating, recombinant, live RSV is capable of infecting one or more host cells when administered to a subject, but generates no progeny or generates progeny that are unable to disseminate.

13. The non-disseminating, recombinant, live RSV of claim 10, wherein the non-disseminating, recombinant, live RSV comprises N, G and F proteins expressed by the RSV genome which lacks a gene encoding an M protein.

14. The non-disseminating, recombinant, live RSV of claim 10, wherein the non-disseminating, recombinant, live RSV is a human RSV.

15. The non-disseminating recombinant, live RSV of claim 10, wherein viral RNA replication and transcription are not attenuated.

* * * * *

SEQUENCE LISTING

```
<160> NUMBER OF SEQ ID NOS: 29

<210> SEQ ID NO 1
<211> LENGTH: 771
<212> TYPE: DNA
<213> ORGANISM: respiratory syncytial virus

<400> SEQUENCE: 1

atggaaacat acgtgaacaa gcttcacgaa ggctccacat acacagctgc tgttcaatac     60

aatgtcttag aaaaagacga tgaccctgca tcacttacaa tatgggtgcc catgttccaa    120

tcatctatgc cagcagattt acttataaaa gaactagcta atgtcaacat actagtgaaa    180

caaatatcca cacccaaggg accttcacta agagtcatga taaactcaag aagtgcagtg    240

ctagcacaaa tgcccagcaa atttaccata tgcgctaatg tgtccttgga tgaaagaagc    300

aaactagcat atgatgtaac cacaccctgt gaaatcaagg catgtagtct aacatgccta    360

aaatcaaaaa atatgttgac tacagttaaa gatctcacta tgaagacact caaccctaca    420

catgatatta ttgctttatg tgaatttgaa aacatagtaa catcaaaaaa agtcataata    480

ccaacatacc taagatccat cagtgtcaga aataaagatc tgaacacact tgaaaatata    540

acaaccactg aattcaaaaa tgctatcaca aatgcaaaaa tcatccctta ctcaggatta    600

ctattagtca tcacagtgac tgacaacaaa ggagcattca aatacataaa gccacaaagt    660

caattcatag tagatcttgg agcttaccta gaaaaagaaa gtatatatta tgttaccaca    720

aattggaagc acacagctac acgatttgca atcaaaccca tggaagatta a             771

<210> SEQ ID NO 2
<211> LENGTH: 771
<212> TYPE: DNA
<213> ORGANISM: respiratory syncytial virus

<400> SEQUENCE: 2

atggagacct acgtgaacaa gctgcacgag ggcagcacct acaccgccgc cgtgcagtac     60

aacgtgctgg agaaggacga cgaccccgcc agcctgacca tctgggtgcc catgttccag    120

agcagcatgc ccgccgacct gctgatcaag gagctggcca acgtgaacat cctggtgaag    180

cagatcagca cccccaaggg gcctagcctg cgcgtgatga tcaacagccg cagcgccgtg    240

ctggcccaga tgcccagcaa gttcaccatc tgcgccaacg tgagcctgga cgagcgcagc    300
```

-continued

```
aagctggcct acgacgtgac cacccccctgc gagatcaagg cctgcagcct gacctgcctg    360

aagagcaaga acatgctgac caccgtgaag gacctgacca tgaagaccct gaaccccacc    420

cacgacatca tcgccctgtg cgagttcgag aacatcgtga ccagcaagaa agtgatcatc    480

cccacctacc tgcgcagcat cagcgtgcgc aacaaggacc tgaacaccct ggagaacatc    540

accaccaccg agttcaagaa cgccatcacc aacgccaaga tcatccccta cagcggcctg    600

ctgctggtga tcaccgtgac cgacaacaag ggcgccttca agtacatcaa gccccagagc    660

cagttcatcg tggacctggg cgcctacctg gagaaggaga gcatctacta cgtgaccacc    720

aactggaagc acaccgccac ccgcttcgcc atcaagccta tggaggacta a             771


<210> SEQ ID NO 3
<211> LENGTH: 256
<212> TYPE: PRT
<213> ORGANISM: respiratory syncytial virus

<400> SEQUENCE: 3

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 4
<211> LENGTH: 265
<212> TYPE: PRT
<213> ORGANISM: Artificial Sequence
<220> FEATURE:
<223> OTHER INFORMATION: Synthetic mutant of M protein
```

<400> SEQUENCE: 4

```
Met Ser Trp Lys Asp Ala Ser Gly Trp Ser Glu Thr Tyr Val Asn Lys
1               5                   10                  15

Leu His Glu Gly Ser Thr Tyr Thr Ala Ala Val Gln Tyr Asn Val Leu
            20                  25                  30

Glu Lys Asp Asp Asp Pro Ala Ser Leu Thr Ile Trp Val Pro Met Phe
        35                  40                  45

Gln Ser Ser Met Pro Ala Asp Leu Leu Ile Lys Glu Leu Ala Asn Val
    50                  55                  60

Asn Ile Leu Val Lys Gln Ile Ser Thr Pro Lys Gly Pro Ser Leu Arg
65                  70                  75                  80

Val Met Ile Asn Ser Arg Ser Ala Val Leu Ala Gln Met Pro Ser Lys
                85                  90                  95

Phe Thr Ile Cys Ala Asn Val Ser Leu Asp Glu Arg Ser Lys Leu Ala
            100                 105                 110

Tyr Asp Val Thr Thr Pro Cys Glu Ile Lys Ala Cys Ser Leu Thr Cys
        115                 120                 125

Leu Lys Ser Lys Asn Met Leu Thr Thr Val Lys Asp Leu Thr Met Lys
    130                 135                 140

Thr Leu Asn Pro Thr His Asp Ile Ile Ala Leu Cys Glu Phe Glu Asn
145                 150                 155                 160

Ile Val Thr Ser Lys Lys Val Ile Ile Pro Thr Tyr Leu Arg Ser Ile
                165                 170                 175

Ser Val Arg Asn Lys Asp Leu Asn Thr Leu Glu Asn Ile Thr Thr Thr
            180                 185                 190

Glu Phe Lys Asn Ala Ile Thr Asn Ala Lys Ile Ile Pro Tyr Ser Gly
        195                 200                 205

Leu Leu Leu Val Ile Thr Val Thr Asp Asn Lys Gly Ala Phe Lys Tyr
    210                 215                 220

Ile Lys Pro Gln Ser Gln Phe Ile Val Asp Leu Gly Ala Tyr Leu Glu
225                 230                 235                 240

Lys Glu Ser Ile Tyr Tyr Val Thr Thr Asn Trp Lys His Thr Ala Thr
                245                 250                 255

Arg Phe Ala Ile Lys Pro Met Glu Asp
            260                 265
```

<210> SEQ ID NO 5
<211> LENGTH: 265
<212> TYPE: PRT
<213> ORGANISM: Artificial Sequence
<220> FEATURE:
<223> OTHER INFORMATION: Synthetic mutant of M protein

<400> SEQUENCE: 5

```
Met Glu Thr Tyr Val Asn Lys Leu His Glu Ser Trp Lys Asp Ala Ser
1               5                   10                  15

Gly Trp Ser Gly Ser Thr Tyr Thr Ala Ala Val Gln Tyr Asn Val Leu
            20                  25                  30

Glu Lys Asp Asp Asp Pro Ala Ser Leu Thr Ile Trp Val Pro Met Phe
        35                  40                  45

Gln Ser Ser Met Pro Ala Asp Leu Leu Ile Lys Glu Leu Ala Asn Val
    50                  55                  60

Asn Ile Leu Val Lys Gln Ile Ser Thr Pro Lys Gly Pro Ser Leu Arg
65                  70                  75                  80
```

-continued

```
Val Met Ile Asn Ser Arg Ser Ala Val Leu Ala Gln Met Pro Ser Lys
                85                  90                  95

Phe Thr Ile Cys Ala Asn Val Ser Leu Asp Glu Arg Ser Lys Leu Ala
            100                 105                 110

Tyr Asp Val Thr Thr Pro Cys Glu Ile Lys Ala Cys Ser Leu Thr Cys
        115                 120                 125

Leu Lys Ser Lys Asn Met Leu Thr Thr Val Lys Asp Leu Thr Met Lys
    130                 135                 140

Thr Leu Asn Pro Thr His Asp Ile Ile Ala Leu Cys Glu Phe Glu Asn
145                 150                 155                 160

Ile Val Thr Ser Lys Lys Val Ile Ile Pro Thr Tyr Leu Arg Ser Ile
                165                 170                 175

Ser Val Arg Asn Lys Asp Leu Asn Thr Leu Glu Asn Ile Thr Thr Thr
            180                 185                 190

Glu Phe Lys Asn Ala Ile Thr Asn Ala Lys Ile Ile Pro Tyr Ser Gly
        195                 200                 205

Leu Leu Leu Val Ile Thr Val Thr Asp Asn Lys Gly Ala Phe Lys Tyr
    210                 215                 220

Ile Lys Pro Gln Ser Gln Phe Ile Val Asp Leu Gly Ala Tyr Leu Glu
225                 230                 235                 240

Lys Glu Ser Ile Tyr Tyr Val Thr Thr Asn Trp Lys His Thr Ala Thr
                245                 250                 255

Arg Phe Ala Ile Lys Pro Met Glu Asp
            260                 265


<210> SEQ ID NO 6
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 6

Met Ala Ala Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175
```

Leu Glu Asn Ile Thr Thr Thr Glu Phe Lys Asn Ala Ile Thr Asn Ala
180 185 190

Lys Ile Ile Pro Tyr Ser Gly Leu Leu Leu Val Ile Thr Val Thr Asp
195 200 205

Asn Lys Gly Ala Phe Lys Tyr Ile Lys Pro Gln Ser Gln Phe Ile Val
210 215 220

Asp Leu Gly Ala Tyr Leu Glu Lys Glu Ser Ile Tyr Tyr Val Thr Thr
225 230 235 240

Asn Trp Lys His Thr Ala Thr Arg Phe Ala Ile Lys Pro Met Glu Asp
245 250 255

<210> SEQ ID NO 7
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 7

Met Glu Thr Ala Ala Asn Lys Leu His Glu Gly Ser Thr Tyr Thr Ala
1 5 10 15

Ala Val Gln Tyr Asn Val Leu Glu Lys Asp Asp Asp Pro Ala Ser Leu
20 25 30

Thr Ile Trp Val Pro Met Phe Gln Ser Ser Met Pro Ala Asp Leu Leu
35 40 45

Ile Lys Glu Leu Ala Asn Val Asn Ile Leu Val Lys Gln Ile Ser Thr
50 55 60

Pro Lys Gly Pro Ser Leu Arg Val Met Ile Asn Ser Arg Ser Ala Val
65 70 75 80

Leu Ala Gln Met Pro Ser Lys Phe Thr Ile Cys Ala Asn Val Ser Leu
85 90 95

Asp Glu Arg Ser Lys Leu Ala Tyr Asp Val Thr Thr Pro Cys Glu Ile
100 105 110

Lys Ala Cys Ser Leu Thr Cys Leu Lys Ser Lys Asn Met Leu Thr Thr
115 120 125

Val Lys Asp Leu Thr Met Lys Thr Leu Asn Pro Thr His Asp Ile Ile
130 135 140

Ala Leu Cys Glu Phe Glu Asn Ile Val Thr Ser Lys Lys Val Ile Ile
145 150 155 160

Pro Thr Tyr Leu Arg Ser Ile Ser Val Arg Asn Lys Asp Leu Asn Thr
165 170 175

Leu Glu Asn Ile Thr Thr Thr Glu Phe Lys Asn Ala Ile Thr Asn Ala
180 185 190

Lys Ile Ile Pro Tyr Ser Gly Leu Leu Leu Val Ile Thr Val Thr Asp
195 200 205

Asn Lys Gly Ala Phe Lys Tyr Ile Lys Pro Gln Ser Gln Phe Ile Val
210 215 220

Asp Leu Gly Ala Tyr Leu Glu Lys Glu Ser Ile Tyr Tyr Val Thr Thr
225 230 235 240

Asn Trp Lys His Thr Ala Thr Arg Phe Ala Ile Lys Pro Met Glu Asp
245 250 255

<210> SEQ ID NO 8
<211> LENGTH: 256
<212> TYPE: PRT
<213> ORGANISM: Artificial Sequence
<220> FEATURE:

<223> OTHER INFORMATION: Synthetic mutant of M protein

<400> SEQUENCE: 8

```
Met Glu Thr Tyr Val Ala Ala Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255
```

<210> SEQ ID NO 9
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 9

```
Met Glu Thr Tyr Val Asn Lys Ala Ala Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95
```

```
Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 10
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 10

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ala Ala Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205
```

```
Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 11
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 11

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Ala Ala Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 12
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 12

Met Glu Thr Tyr Val Asn Lys Leu His Glu Gly Ser Thr Tyr Thr Ala
```

-continued

```
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Ala Ala Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 13
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 13

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ala Ala Asn Met Leu Thr Thr
```

```
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 14
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 14

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Ala Ala Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
```

225 230 235 240

Asn Trp Lys His Thr Ala Thr Arg Phe Ala Ile Lys Pro Met Glu Asp
245 250 255

<210> SEQ ID NO 15
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 15

Met Glu Thr Tyr Val Asn Lys Leu His Glu Gly Ser Thr Tyr Thr Ala
1 5 10 15

Ala Val Gln Tyr Asn Val Leu Glu Lys Asp Asp Asp Pro Ala Ser Leu
20 25 30

Thr Ile Trp Val Pro Met Phe Gln Ser Ser Met Pro Ala Asp Leu Leu
35 40 45

Ile Lys Glu Leu Ala Asn Val Asn Ile Leu Val Lys Gln Ile Ser Thr
50 55 60

Pro Lys Gly Pro Ser Leu Arg Val Met Ile Asn Ser Arg Ser Ala Val
65 70 75 80

Leu Ala Gln Met Pro Ser Lys Phe Thr Ile Cys Ala Asn Val Ser Leu
85 90 95

Asp Glu Arg Ser Lys Leu Ala Tyr Asp Val Thr Thr Pro Cys Glu Ile
100 105 110

Lys Ala Cys Ser Leu Thr Cys Leu Lys Ser Lys Asn Met Ala Ala Thr
115 120 125

Val Lys Asp Leu Thr Met Lys Thr Leu Asn Pro Thr His Asp Ile Ile
130 135 140

Ala Leu Cys Glu Phe Glu Asn Ile Val Thr Ser Lys Lys Val Ile Ile
145 150 155 160

Pro Thr Tyr Leu Arg Ser Ile Ser Val Arg Asn Lys Asp Leu Asn Thr
165 170 175

Leu Glu Asn Ile Thr Thr Thr Glu Phe Lys Asn Ala Ile Thr Asn Ala
180 185 190

Lys Ile Ile Pro Tyr Ser Gly Leu Leu Leu Val Ile Thr Val Thr Asp
195 200 205

Asn Lys Gly Ala Phe Lys Tyr Ile Lys Pro Gln Ser Gln Phe Ile Val
210 215 220

Asp Leu Gly Ala Tyr Leu Glu Lys Glu Ser Ile Tyr Tyr Val Thr Thr
225 230 235 240

Asn Trp Lys His Thr Ala Thr Arg Phe Ala Ile Lys Pro Met Glu Asp
245 250 255

<210> SEQ ID NO 16
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 16

Met Glu Thr Tyr Val Asn Lys Leu His Glu Gly Ser Thr Tyr Thr Ala
1 5 10 15

Ala Val Gln Tyr Asn Val Leu Glu Lys Asp Asp Asp Pro Ala Ser Leu
20 25 30

```
Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Ala
        115                 120                 125

Ala Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 17
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 17

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Ala Ala Leu Thr Met Lys Thr Leu Asn Pro Thr His Asp Ile Ile
    130                 135                 140
```

```
Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 18
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 18

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Ala Ala Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255
```

<210> SEQ ID NO 19
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 19

```
Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Ala Ala Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255
```

<210> SEQ ID NO 20
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 20

```
Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60
```

Pro Lys Gly Pro Ser Leu Arg Val Met Ile Asn Ser Arg Ser Ala Val
65 70 75 80

Leu Ala Gln Met Pro Ser Lys Phe Thr Ile Cys Ala Asn Val Ser Leu
85 90 95

Asp Glu Arg Ser Lys Leu Ala Tyr Asp Val Thr Thr Pro Cys Glu Ile
100 105 110

Lys Ala Cys Ser Leu Thr Cys Leu Lys Ser Lys Asn Met Leu Thr Thr
115 120 125

Val Lys Asp Leu Thr Met Lys Ala Ala Asn Pro Thr His Asp Ile Ile
130 135 140

Ala Leu Cys Glu Phe Glu Asn Ile Val Thr Ser Lys Lys Val Ile Ile
145 150 155 160

Pro Thr Tyr Leu Arg Ser Ile Ser Val Arg Asn Lys Asp Leu Asn Thr
165 170 175

Leu Glu Asn Ile Thr Thr Thr Glu Phe Lys Asn Ala Ile Thr Asn Ala
180 185 190

Lys Ile Ile Pro Tyr Ser Gly Leu Leu Leu Val Ile Thr Val Thr Asp
195 200 205

Asn Lys Gly Ala Phe Lys Tyr Ile Lys Pro Gln Ser Gln Phe Ile Val
210 215 220

Asp Leu Gly Ala Tyr Leu Glu Lys Glu Ser Ile Tyr Tyr Val Thr Thr
225 230 235 240

Asn Trp Lys His Thr Ala Thr Arg Phe Ala Ile Lys Pro Met Glu Asp
245 250 255

<210> SEQ ID NO 21
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 21

Met Glu Thr Tyr Val Asn Lys Leu His Glu Gly Ser Thr Tyr Thr Ala
1 5 10 15

Ala Val Gln Tyr Asn Val Leu Glu Lys Asp Asp Asp Pro Ala Ser Leu
20 25 30

Thr Ile Trp Val Pro Met Phe Gln Ser Ser Met Pro Ala Asp Leu Leu
35 40 45

Ile Lys Glu Leu Ala Asn Val Asn Ile Leu Val Lys Gln Ile Ser Thr
50 55 60

Pro Lys Gly Pro Ser Leu Arg Val Met Ile Asn Ser Arg Ser Ala Val
65 70 75 80

Leu Ala Gln Met Pro Ser Lys Phe Thr Ile Cys Ala Asn Val Ser Leu
85 90 95

Asp Glu Arg Ser Lys Leu Ala Tyr Asp Val Thr Thr Pro Cys Glu Ile
100 105 110

Lys Ala Cys Ser Leu Thr Cys Leu Lys Ser Lys Asn Met Leu Thr Thr
115 120 125

Val Lys Asp Leu Thr Met Lys Thr Leu Ala Ala Thr His Asp Ile Ile
130 135 140

Ala Leu Cys Glu Phe Glu Asn Ile Val Thr Ser Lys Lys Val Ile Ile
145 150 155 160

Pro Thr Tyr Leu Arg Ser Ile Ser Val Arg Asn Lys Asp Leu Asn Thr
165 170 175

```
Leu Glu Asn Ile Thr Thr Thr Glu Phe Lys Asn Ala Ile Thr Asn Ala
            180                185                190

Lys Ile Ile Pro Tyr Ser Gly Leu Leu Leu Val Ile Thr Val Thr Asp
        195                200                205

Asn Lys Gly Ala Phe Lys Tyr Ile Lys Pro Gln Ser Gln Phe Ile Val
    210                215                220

Asp Leu Gly Ala Tyr Leu Glu Lys Glu Ser Ile Tyr Tyr Val Thr Thr
225                230                235                240

Asn Trp Lys His Thr Ala Thr Arg Phe Ala Ile Lys Pro Met Glu Asp
                245                250                255
```

<210> SEQ ID NO 22
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 22

```
Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                105                110

Lys Ala Cys Ser Leu Thr Cys Leu Lys Ser Lys Asn Met Leu Thr Thr
        115                120                125

Val Lys Asp Leu Thr Met Lys Thr Leu Asn Pro Ala Ala Asp Ile Ile
    130                135                140

Ala Leu Cys Glu Phe Glu Asn Ile Val Thr Ser Lys Lys Val Ile Ile
145                150                155                160

Pro Thr Tyr Leu Arg Ser Ile Ser Val Arg Asn Lys Asp Leu Asn Thr
                165                170                175

Leu Glu Asn Ile Thr Thr Thr Glu Phe Lys Asn Ala Ile Thr Asn Ala
            180                185                190

Lys Ile Ile Pro Tyr Ser Gly Leu Leu Leu Val Ile Thr Val Thr Asp
        195                200                205

Asn Lys Gly Ala Phe Lys Tyr Ile Lys Pro Gln Ser Gln Phe Ile Val
    210                215                220

Asp Leu Gly Ala Tyr Leu Glu Lys Glu Ser Ile Tyr Tyr Val Thr Thr
225                230                235                240

Asn Trp Lys His Thr Ala Thr Arg Phe Ala Ile Lys Pro Met Glu Asp
                245                250                255
```

<210> SEQ ID NO 23
<211> LENGTH: 256
<212> TYPE: PRT
<213> ORGANISM: Artificial Sequence

```
<220> FEATURE:
<223> OTHER INFORMATION: Synthetic mutant of M protein

<400> SEQUENCE: 23

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Ala Ala Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 24
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 24

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
```

-continued

```
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ala
    130                 135                 140

Gly Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 25
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 25

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Ala Ala Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
```

```
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 26
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 26

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Ala Ala Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 27
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 27
```

-continued

```
Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Ala Ala Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255
```

<210> SEQ ID NO 28
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 28

```
Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110
```

```
Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ala Ala Thr Ser Lys Lys Val Ile Ile
145                 150                 155                 160

Pro Thr Tyr Leu Arg Ser Ile Ser Val Arg Asn Lys Asp Leu Asn Thr
            165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
            245                 250                 255


<210> SEQ ID NO 29
<211> LENGTH: 256
<212> TYPE: PRT
<213> ORGANISM: Artificial Sequence
<220> FEATURE:
<223> OTHER INFORMATION: Synthetic mutant of M protein

<400> SEQUENCE: 29

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Ala Ala Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220
```

-continued

```
Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255
```